United States Patent
Chew et al.

(10) Patent No.: US 7,905,913 B2
(45) Date of Patent: *Mar. 15, 2011

(54) APPARATUS AND METHODS FOR DELIVERY OF MULTIPLE DISTRIBUTED STENTS

(75) Inventors: Sunmi Chew, San Jose, CA (US); Bernard Andreas, Redwood City, CA (US); Hanson S. Gifford, III, Woodside, CA (US); Ron French, Santa Clara, CA (US); Mark E. Deem, Mountain View, CA (US); Allan Will, Atherton, CA (US)

(73) Assignee: Xtent, Inc., Menlo Park, CA (US)

( * ) Notice: Subject to any disclaimer, the term of this patent is extended or adjusted under 35 U.S.C. 154(b) by 1056 days.

This patent is subject to a terminal disclaimer.

(21) Appl. No.: 11/563,847

(22) Filed: Nov. 28, 2006

(65) Prior Publication Data
US 2007/0100424 A1    May 3, 2007

Related U.S. Application Data

(63) Continuation of application No. 10/306,813, filed on Nov. 27, 2002, now abandoned.

(60) Provisional application No. 60/364,389, filed on Mar. 13, 2002, provisional application No. 60/336,967, filed on Dec. 3, 2001.

(51) Int. Cl.
*A61F 2/06* (2006.01)
(52) U.S. Cl. ...................................... 623/1.11
(58) Field of Classification Search ................. 623/1.11, 623/1.12, 1.15, 1.16; 606/191–198; 604/101.01, 604/101.02, 1.16
See application file for complete search history.

(56) References Cited

U.S. PATENT DOCUMENTS

| | | | |
|---|---|---|---|
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,733,665 A | 3/1988 | Palmaz |

(Continued)

FOREIGN PATENT DOCUMENTS

EP   203945 B2   12/1986

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Kevin T Truong
(74) *Attorney, Agent, or Firm* — Kilpatrick Townsend & Stockton LLP

(57) ABSTRACT

Blood vessels and other body lumens are stented using multiple, discreet stent structures. Stent structures may be balloon expandable or self-expanding and are delivered by a delivery catheter which is repositioned to spaced-apart delivery sights. By coating the stents with particular biologically active substances, hyperplasia within and between the implanted stents can be inhibited. An exemplary delivery catheter comprises a catheter body having both a pusher rod for advancing the stents relative to a sheath and a reciprocatable delivery catheter for implanting the stents.

21 Claims, 18 Drawing Sheets

U.S. PATENT DOCUMENTS

| | | | |
|---|---|---|---|
| 4,739,762 A | 4/1988 | Palmaz | |
| 4,762,129 A | 8/1988 | Bonzel | |
| 4,775,337 A | 10/1988 | Van Wagener et al. | |
| 4,776,337 A | 10/1988 | Palmaz | |
| 4,886,062 A | 12/1989 | Wiktor | |
| 4,988,356 A | 1/1991 | Crittenden et al. | |
| 4,994,066 A | 2/1991 | Voss | |
| 4,994,069 A | 2/1991 | Ritchart et al. | |
| 5,013,318 A | 5/1991 | Spranza, III | |
| 5,040,548 A | 8/1991 | Yock | |
| 5,092,877 A | 3/1992 | Pinchuk | |
| 5,102,417 A | 4/1992 | Palmaz | |
| 5,104,404 A | 4/1992 | Wolff | |
| 5,135,535 A | 8/1992 | Kramer | |
| 5,192,297 A * | 3/1993 | Hull | 623/1.11 |
| 5,195,984 A | 3/1993 | Schatz | |
| 5,201,757 A * | 4/1993 | Heyn et al. | 606/198 |
| 5,217,495 A | 6/1993 | Kaplan et al. | |
| 5,226,913 A | 7/1993 | Pinchuk | |
| 5,246,421 A | 9/1993 | Saab | |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,334,187 A | 8/1994 | Fischell et al. | |
| 5,421,955 A | 6/1995 | Lau et al. | |
| 5,458,615 A | 10/1995 | Klemm et al. | |
| 5,478,349 A | 12/1995 | Nicholas | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,527,354 A | 6/1996 | Fontaine et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,775 A | 5/1997 | Jackson et al. | |
| 5,634,928 A | 6/1997 | Fischell et al. | |
| 5,662,675 A | 9/1997 | Polanskyj Stockert et al. | |
| 5,676,654 A | 10/1997 | Ellis et al. | |
| 5,683,451 A | 11/1997 | Lenker et al. | |
| 5,697,948 A | 12/1997 | Marin et al. | |
| 5,702,418 A | 12/1997 | Ravenscroft | |
| 5,709,701 A | 1/1998 | Parodi | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,749,848 A | 5/1998 | Jang et al. | |
| 5,749,921 A | 5/1998 | Lenker et al. | |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,092 A | 12/1998 | Heller et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,922,020 A | 7/1999 | Klein et al. | |
| 5,961,536 A | 10/1999 | Mickley et al. | |
| 5,968,069 A | 10/1999 | Dusbabek et al. | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 6,007,517 A | 12/1999 | Anderson | |
| 6,022,359 A | 2/2000 | Frantzen | |
| 6,033,434 A | 3/2000 | Borghi | |
| 6,039,721 A | 3/2000 | Johnson et al. | |
| 6,042,589 A | 3/2000 | Marianne | |
| 6,056,722 A | 5/2000 | Jayaraman | |
| 6,066,155 A | 5/2000 | Amann et al. | |
| 6,068,655 A | 5/2000 | Seguin et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,143,016 A | 11/2000 | Bleam et al. | |
| 6,165,167 A | 12/2000 | Delaloye | |
| 6,179,878 B1 | 1/2001 | Duerig | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,612 B1 | 7/2001 | Hieshima | |
| 6,254,628 B1 | 7/2001 | Wallace et al. | |
| 6,258,117 B1 | 7/2001 | Camrud et al. | |
| 6,267,783 B1 | 7/2001 | Letendre et al. | |
| 6,273,895 B1 | 8/2001 | Pinchuk et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,277 B1 | 11/2001 | Rudnick et al. | |
| 6,325,823 B1 | 12/2001 | Horzewski et al. | |
| 6,357,104 B1 | 3/2002 | Myers | |
| 6,375,676 B1 | 4/2002 | Cox | |
| 6,383,171 B1 | 5/2002 | Gifford et al. | |
| 6,419,693 B1 | 7/2002 | Fariabi | |
| 6,451,025 B1 | 9/2002 | Jervis | |
| 6,451,050 B1 | 9/2002 | Rudakov et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,488,702 B1 | 12/2002 | Besselink | |
| 6,511,468 B1 | 1/2003 | Cragg et al. | |
| 6,520,987 B1 | 2/2003 | Plante | |
| 6,527,789 B1 | 3/2003 | Lau et al. | |
| 6,527,799 B2 | 3/2003 | Shanley | |
| 6,555,157 B1 | 4/2003 | Hossainy | |
| 6,575,993 B1 | 6/2003 | Yock | |
| 6,582,394 B1 | 6/2003 | Reiss et al. | |
| 6,592,549 B2 | 7/2003 | Gerdts et al. | |
| 6,599,296 B1 | 7/2003 | Gillick et al. | |
| 6,602,282 B1 | 8/2003 | Yan | |
| 6,605,062 B1 | 8/2003 | Hurley et al. | |
| 6,645,547 B1 | 11/2003 | Shekalim et al. | |
| 6,656,212 B2 | 12/2003 | Ravenscroft et al. | |
| 6,666,883 B1 | 12/2003 | Seguin et al. | |
| 6,679,909 B2 | 1/2004 | McIntosh et al. | |
| 6,692,465 B2 | 2/2004 | Kramer | |
| 6,702,843 B1 | 3/2004 | Brown | |
| 6,712,827 B2 | 3/2004 | Ellis et al. | |
| 6,712,845 B2 | 3/2004 | Hossainy | |

| | | |
|---|---|---|
| 6,723,071 B2 | 4/2004 | Gerdts et al. |
| 6,743,251 B1 | 6/2004 | Eder |
| 6,800,065 B2 | 10/2004 | Duane et al. |
| 6,849,084 B2 | 2/2005 | Rabkin et al. |
| 2001/0020154 A1 | 9/2001 | Bigus et al. |
| 2001/0020181 A1 | 9/2001 | Layne |
| 2001/0044595 A1 | 11/2001 | Reydel et al. |
| 2002/0037358 A1 | 3/2002 | Barry et al. |
| 2002/0107560 A1 | 8/2002 | Richter |
| 2002/0138132 A1 | 9/2002 | Brown |
| 2002/0151955 A1 | 10/2002 | Tran et al. |
| 2002/0156496 A1 | 10/2002 | Chermoni |
| 2002/0177890 A1 | 11/2002 | Lenker |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0176909 A1 | 9/2003 | Kusleika |
| 2003/0199821 A1 | 10/2003 | Gerdts et al. |
| 2003/0225446 A1 | 12/2003 | Hartley |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0098081 A1 | 5/2004 | Landreville et al. |
| 2004/0186551 A1 | 9/2004 | Kao et al. |
| 2004/0215165 A1 | 10/2004 | Coyle et al. |
| 2004/0215312 A1 | 10/2004 | Andreas |
| 2004/0249435 A1 | 12/2004 | Andreas et al. |
| 2005/0010276 A1 | 1/2005 | Acosta et al. |
| 2005/0038505 A1 | 2/2005 | Shuize et al. |
| 2005/0133164 A1 | 6/2005 | Fischer et al. |
| 2005/0149159 A1 | 7/2005 | Andreas et al. |
| 2005/0288763 A1 | 12/2005 | Andreas et al. |
| 2006/0229700 A1 | 10/2006 | Acosta et al. |
| 2006/0282147 A1 | 12/2006 | Andreas et al. |
| 2006/0282150 A1 | 12/2006 | Olson et al. |

FOREIGN PATENT DOCUMENTS

| | | |
|---|---|---|
| EP | 274129 B1 | 7/1988 |
| EP | 282143 | 9/1988 |
| EP | 0 505 686 | 9/1992 |
| EP | 0 533 960 | 3/1993 |
| EP | 0 596 145 | 5/1997 |
| EP | 947180 | 10/1999 |
| EP | 1266638 B1 | 10/2005 |
| WO | WO 96/33677 | 10/1996 |
| WO | WO 97/46174 | 12/1997 |
| WO | WO 97/48351 | 12/1997 |
| WO | WO 99/01087 A1 | 1/1999 |
| WO | WO 00/15151 | 3/2000 |
| WO | WO 00/32136 | 6/2000 |
| WO | WO 00/41649 A1 | 7/2000 |
| WO | WO 00/50116 | 8/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 | 3/2003 |
| WO | WO 03/047651 | 6/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

* cited by examiner

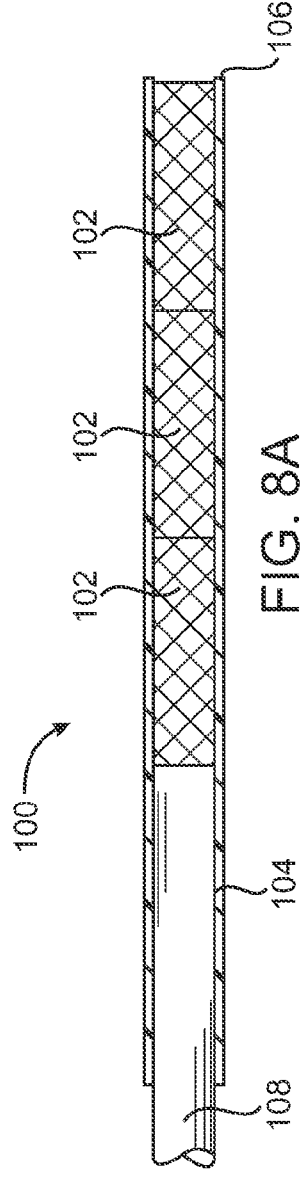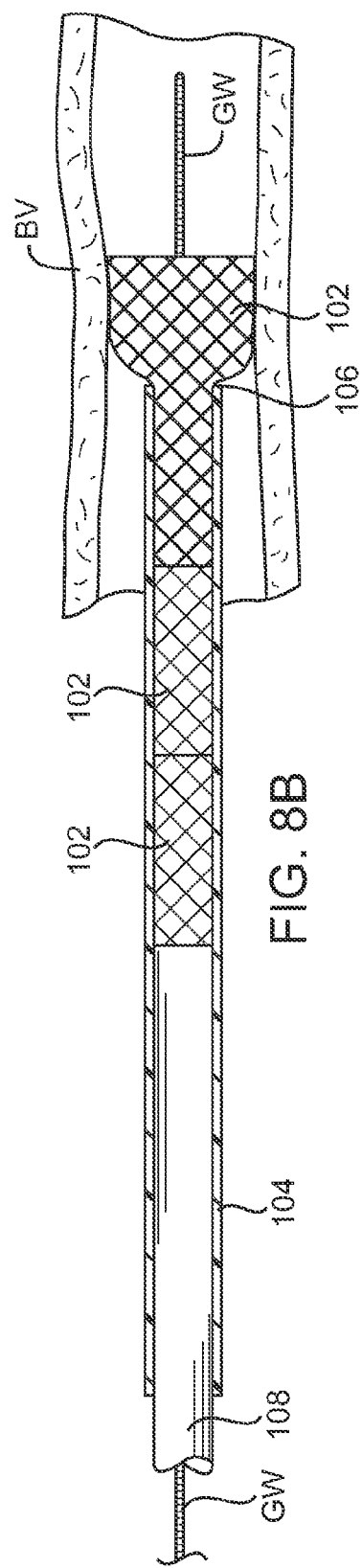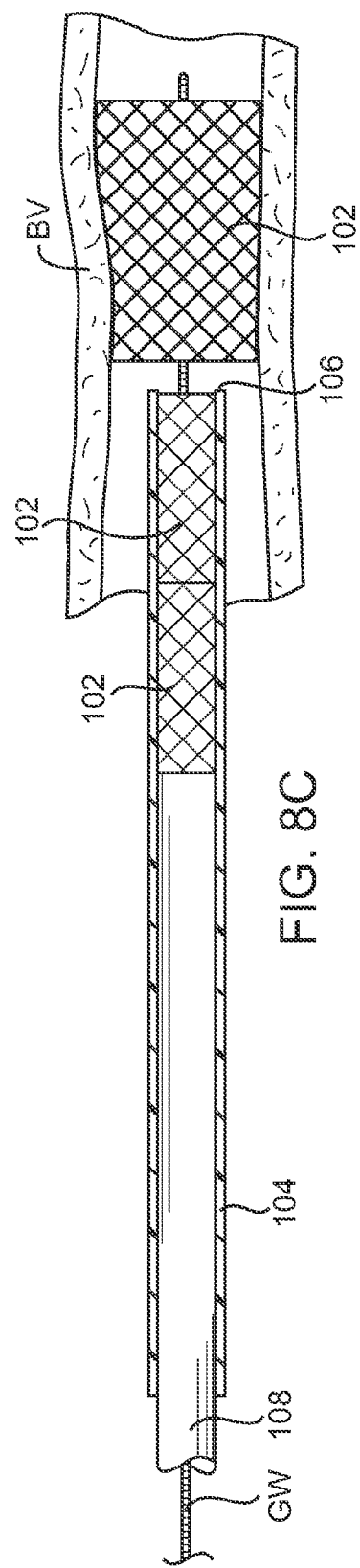

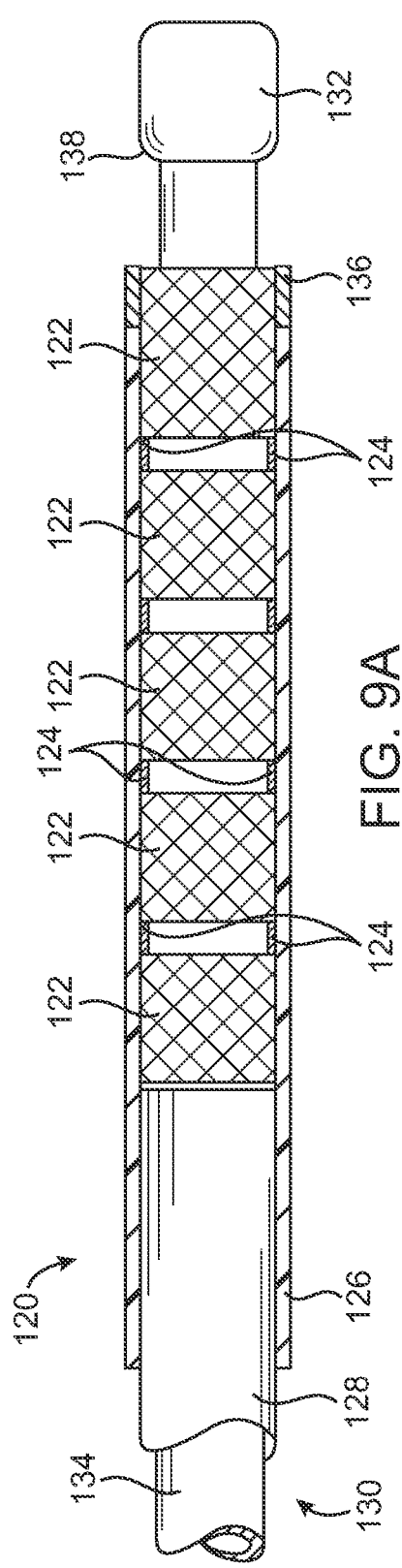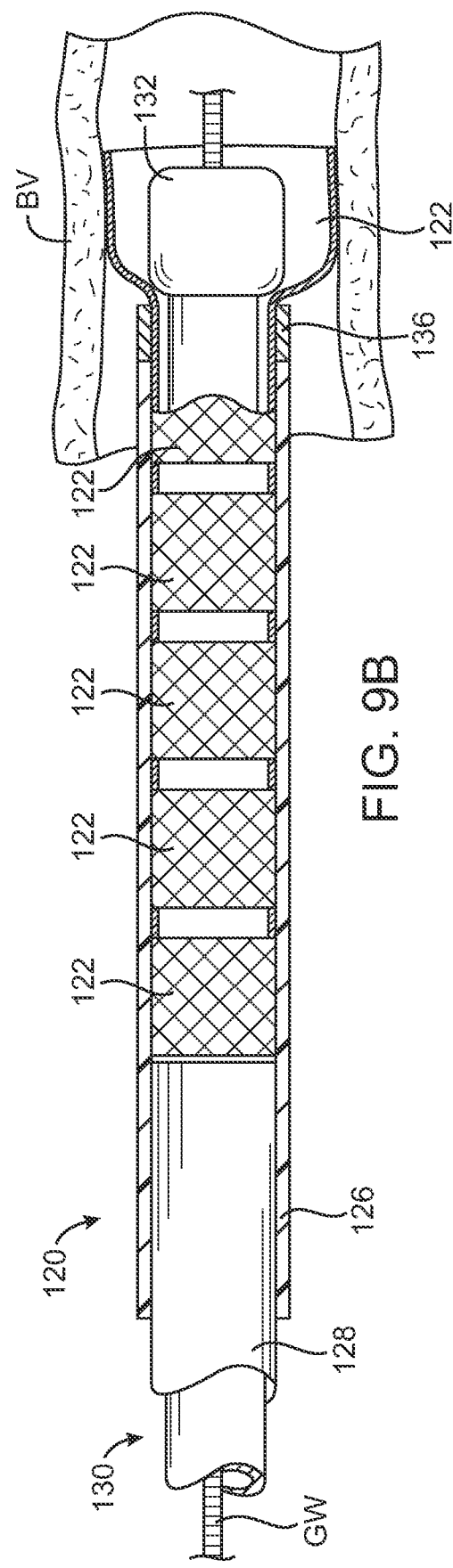

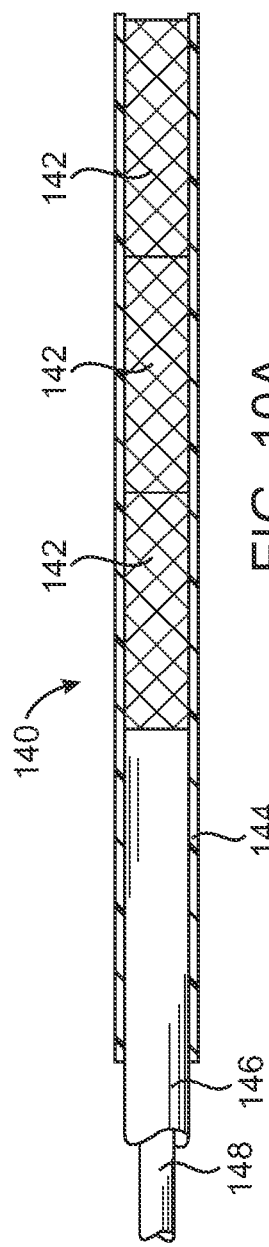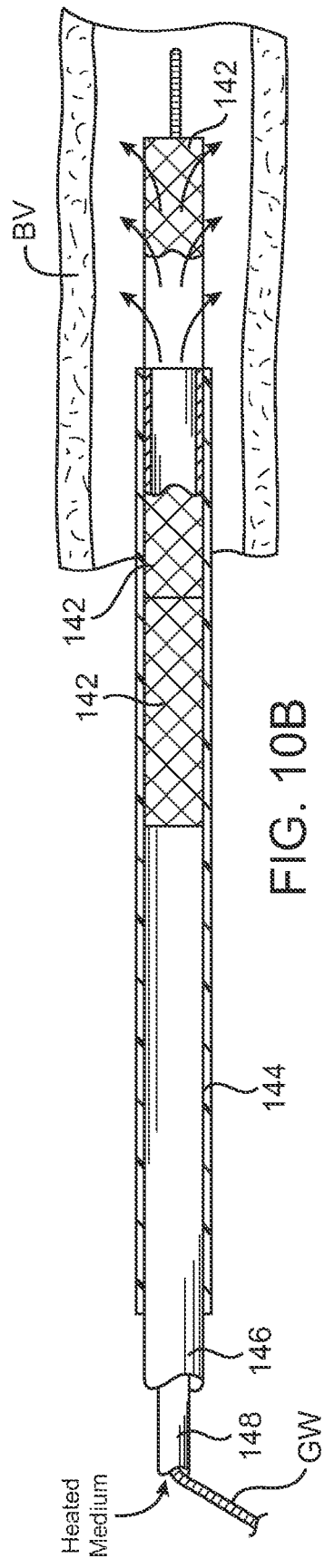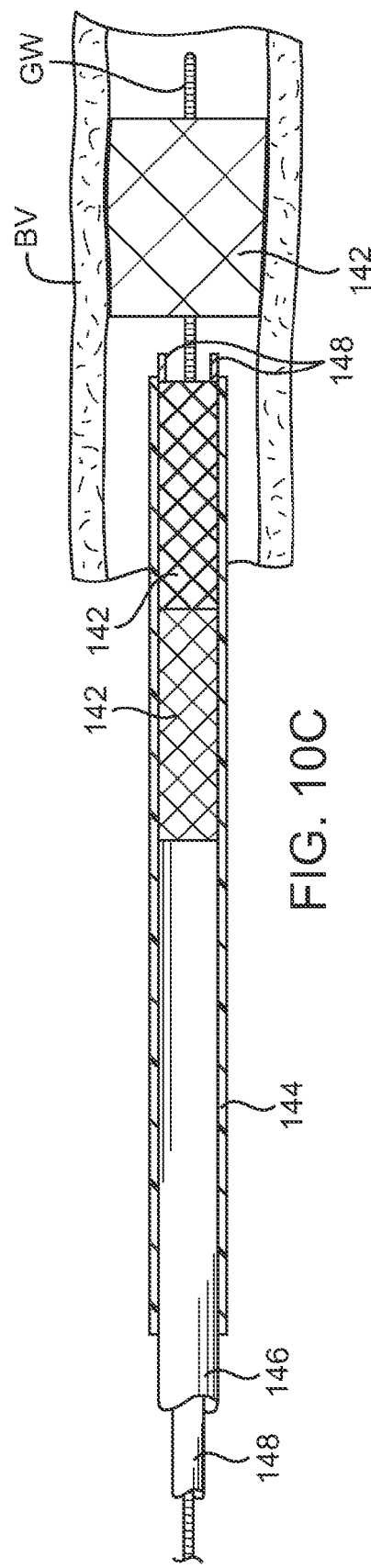

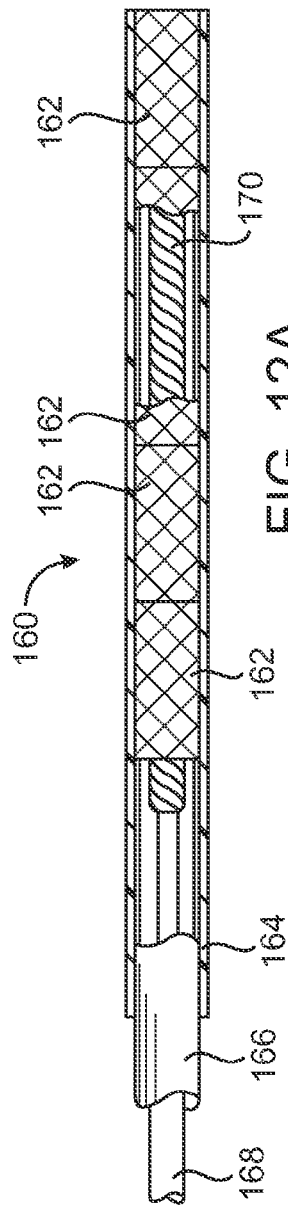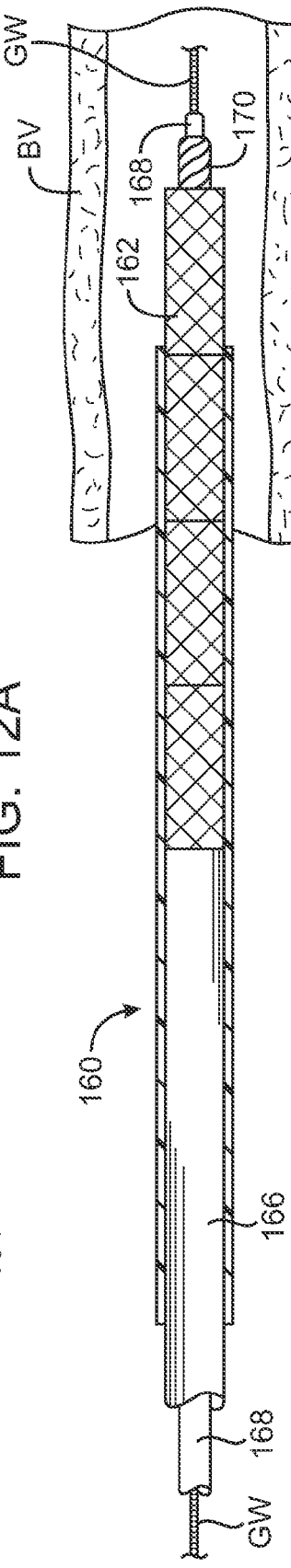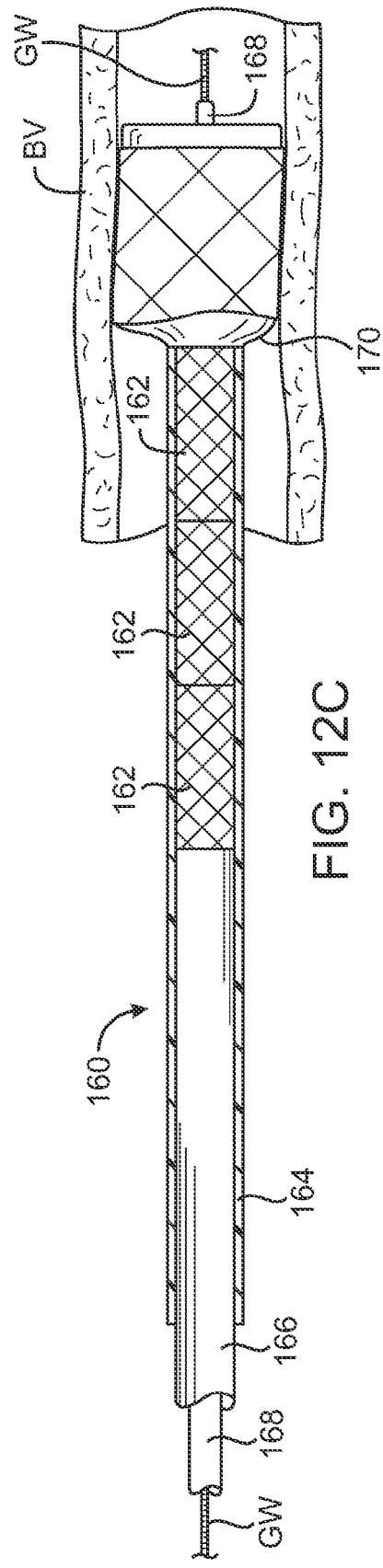

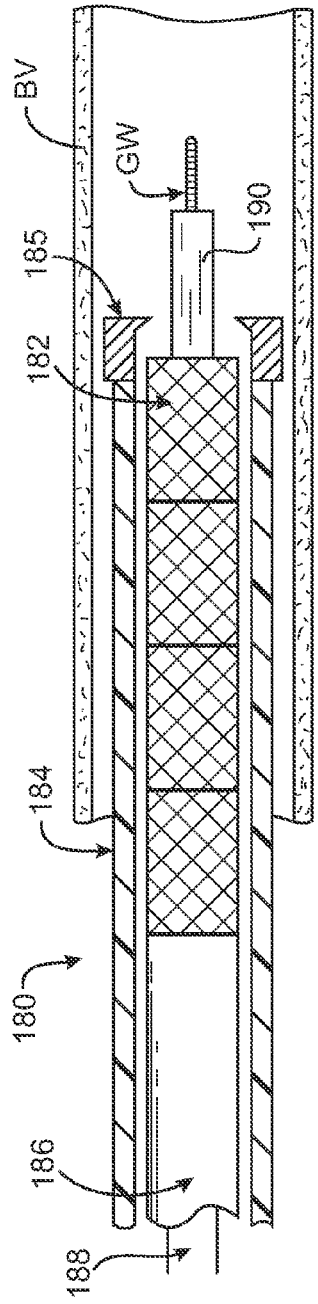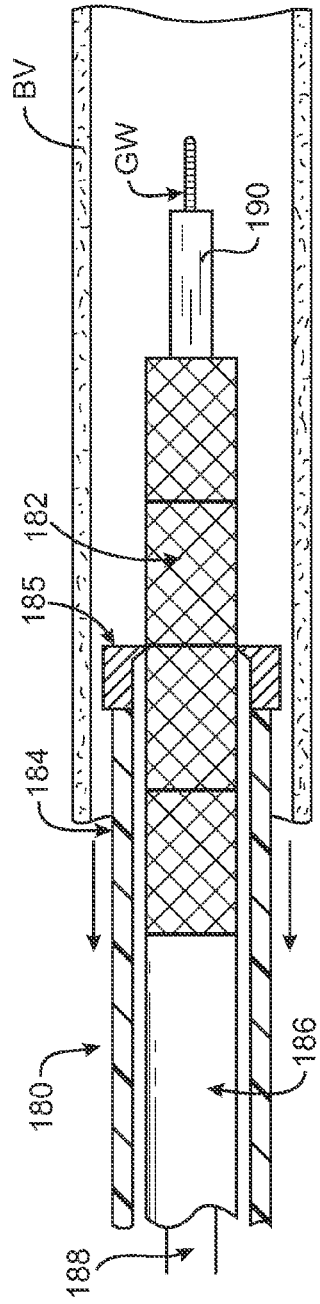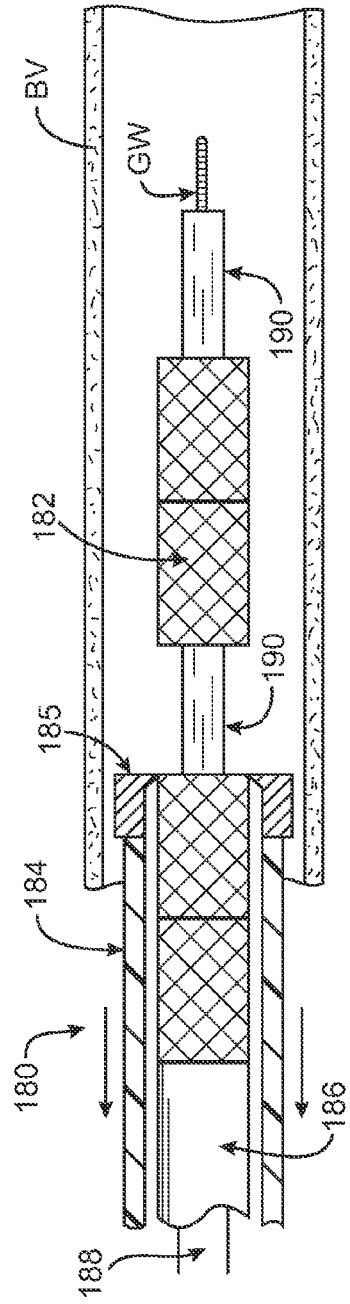

APPARATUS AND METHODS FOR DELIVERY OF MULTIPLE DISTRIBUTED STENTS

CROSS-REFERENCES TO RELATED APPLICATIONS

The present application is a continuation of U.S. patent application Ser. No. 10/306,813, filed on Nov. 27, 2002, which was a non-provisional of U.S. Patent Application Ser. Nos. 60/336,967 filed Dec. 3, 2001, and is also a non-provisional of U.S. Patent Application Ser. No. 60/364,389 filed on Mar. 13, 2002, the full disclosures of which are incorporated herein by reference.

BACKGROUND OF THE INVENTION

1. Field of the Invention

The present invention relates generally to medical devices and methods. More particularly, the present invention relates to apparatus and methods for independently delivering a plurality of luminal prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or, even if survived, can cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that the coating of stents using anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the suggestive use of balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature. In particular, it would be desirable to provide stents, delivery systems, and methods for the treatment of disseminated and variable length stenotic regions within the vasculature. For example, it would be desirable to provide a practical method which permits a physician to optimize the length of the treated vessel which is stented according to the nature of the disease. More specifically, it would be desirable to provide apparatus, systems, and methods for facilitating the delivery of multiple stents and other prostheses to blood vessels or other target body lumens. Such apparatus, systems, and methods should be suitable for delivery of individual stents or prostheses having very short lengths, typically as short as 3 mm or shorter, at multiple contiguous and non-contiguous locations within a body lumen for optimized treatment thereof. At least some of these objectives will be met by the inventions described hereinafter.

2. Description of the Background Art

U.S. Pat. No. 6,258,117 B1 describes a stent having multiple sections connected by separable or frangible connecting regions. Optionally, the connecting regions are severed after the stent structure has been implanted in the blood vessel. U.S. Pat. Nos. 5,571,086; 5,776,141; and 6,143,016 describe an expandable sleeve for placement over a balloon catheter for the delivery of one or two stent structures to the vasculature. U.S. Pat. No. 5,697,948 describes a catheter for delivering stents covered by a sheath.

BRIEF SUMMARY OF THE INVENTION

The present invention provides methods and apparatus for prosthesis placement, such as stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable prostheses and scaffolds which are designed to be intraluminally introduced to a treatment site and expanded in situ to apply a radially outward force against the inner wall of the body lumen at that site. Stents and prostheses commonly comprise an open lattice structure, typically formed from a malleable or elastic metal. When formed from a malleable metal, the stents will typically be expanded by a balloon which causes plastic deformation of the lattice so that it remains opened after deployment. When formed from an elastic metal, including super elastic metals such as nickel-titanium alloys, the lattice structures will usually be radially constrained when delivered and deployed by releasing the structures from such radial constraint so that they "self-expand" at the target site. When the stent or lattice structures are covered with a fabric or polymeric membrane covering, they are commonly referred to as grafts. Grafts may be used for the treatment of aneurysms or other conditions which require placement of a non-permeable or semi-permeable barrier at the treatment site. The terms "prosthesis" and "prostheses" refer broadly to all radially expansible stents, grafts, and other scaffold-like structures which are intended for deployment within body lumens.

The stents and prostheses of the present invention may have any of a variety of common constructions, including helical structures, counterwound helical structures, expandable diamond structures, serpentine structures, or the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980,552; 5,836,964; 5,527,354; 5,421,955; 4,886,062; and 4,776,337, the full disclosures of which are incorporated herein by reference. Preferred structures are described herein with reference to FIGS. 4 and 5.

According to the present invention, the stents which are deployed may have a length of 1 mm or greater, usually 2 mm or greater, and typically of 3 mm or greater, usually being in the range from 1 mm to 100 mm, typically from 2 mm to 50 mm, more typically from 2 mm to 25 mm, and usually from 3 mm to 20 mm. The use of such short stent lengths is advantageous since multiple stents are to be employed.

The methods and apparatus of the present invention will provide for the deployment of a plurality of stents or other prostheses, usually including at least two stents, from a common stent delivery catheter. Usually, the number of delivered stents will be in the range from 2 to 50, typically from 3 to 30, and most typically from 5 to 25. As more stents are placed on the delivery catheter, the individual stent length will often be somewhat less, although this is not necessarily the case in all instances. The multiple prostheses may be deployed individually or in groups of two or more at single or multiple spaced-apart locations in the body lumen or lumens.

In a first aspect of the present invention, a method for stenting an extended length of a body lumen comprises introducing a catheter carrying a plurality of, usually at least two, discrete stents to the body lumen. Usually, the introduction is percutaneous and, in the case of intravascular delivery, uses a conventional introduction technique, such as the Seldinger technique. After reaching a target location, at least a first stent is released from the catheter at that first location. The catheter is then repositioned to a second location, and at least a second stent is released from the catheter at the second location. The catheter is then repositioned to a third location, and at least a third stent is released from the catheter at the third location In addition to deploying stents and other prostheses at spaced-apart locations within a blood vessel or other body lumen, the methods and apparatus in the present invention can be used for delivering one, two, three, or more discrete stents or other prosthesis segments contiguously at a single location within the body lumen. In this way, the length of the prosthesis which is implanted can be selected and modified to accommodate the length of the vessel to be treated. It will be appreciated that with systems which carry 10, 20, 30 or more quite short prostheses or prosthesis segments, the length of the lumen being treated can be tailored very closely from very short to very long with the selectable intervals depending on the length of the prosthesis or prosthesis segment.

The deployment steps can, of course, be repeated a sufficient number of times so that all or at least more of the stents carried by the delivery catheter are delivered to and deployed within the body lumen. A particular advantage of this delivery method is that the discrete stents may be distributed along extended lengths of the body lumen, typically in the range from 1 cm to 2 cm, often in the range from 1 cm to 5 cm, and in many instances even longer. Additionally, the stents may be delivered so as to avoid side branches or other regions where placement of the stent is undesirable. Moreover, with the use of drug-coated stents, it may be possible to place the stents apart by discrete distances, typically from one-half to one millimeter (mm), while still achieving vessel patency and hyperplasia inhibition.

Releasing of the stents from the catheter may be achieved using a balloon to cause balloon expansion of the stent. Alternatively, release of the stent may be achieved by radially constraining an elastic or self-expanding stent within a lumen of the delivery catheter and selectively advancing the stent from the catheter and/or retracting the catheter from over the stent. In one embodiment, a sheath over the stents includes a valve member, or "stent valve," which allows stents to be separated so that a balloon can more accurately inflate deployed stents while other stents remain within the sheath.

In preferred embodiments, the stents are coated with at least one agent, such as an agent which inhibits hyperplasia. The agent may be biologically active or inert. Particular biologically active agents include anti-neoplastic drugs such as paclitaxel, methotrexate, and batimastal; antibiotics such as doxycycline, tetracycline, rapamycin, and actinomycin; immunosuppressant such as dexamethosone, methyl prednisolone, nitric oxide sources such as nitroprussides; estrogen; estradiols; and the like. Biologically inert agents include polyethylene glycol (PEG), collagen, polyglycolic acids (PGA), ceramic material, titanium, gold and the like.

In another aspect, the present invention comprises catheters and apparatus for stenting extended lengths of a body lumen, particularly a blood vessel. The catheters comprise a catheter body having a proximal end and a distal end. At least two discrete stents are carried at or near a distal end of the catheter body. By "discrete," it is meant that the stents are unconnected and can be deployed from the catheter in an unattached manner. (The delivery of attached prostheses is described below.) Deployment of such discrete stents permits the individual stents to be placed at spaced-apart target locations or immediately adjacently within the blood vessel or other body lumen. The catheters further comprise deployment means for deploying the individual stents from the catheter body. For example, the deployment means may comprise one or more balloons for placement and radial expansion of the stents. Alternatively, the deployment means may comprise a pusher or other device for advancing self-expanding stents from the distal end of the catheter body and/or a sheath for selectively retracting over the stents to permit self-expansion. In exemplary embodiments, the catheters will carry at least two discrete stents, at least five discrete stents, and as many as 10 discrete stents, or in some cases, as many as 30 or more discrete stents.

In a particular embodiment, the catheter comprises a single balloon which is reciprocatively mounted within the catheter body and adapted for receiving individual stents thereover. A pusher or other device for successively and controllably loading individual or multiple stents over the balloon is also provided. In this way, the catheter may carry multiple stents and employ the single balloon for positioning and expansion of the stents.

In further embodiments, the stents of the present invention are composed at least partly of a bioabsorbable material, such as polyethylene glycol (PEG), collagen, gelatin, polyglycolic acids (PGA), polylactic acids (PLA), and the like. Optionally, one or more bioactive substances are dispersed in the bioabsorbable material such that the bioactive substance will be released over time as the bioabsorbable material degrades. In a particular embodiment, the bioabsorbable material is formed on or within a scaffold composed on a non-bioabsorbable material, typically stainless steel, Nitinol™, or other conventional stent metal material. Other materials, such as gold (e.g., pure or nearly pure gold), platinum, or the like, may also be used.

In a further aspect of the present invention, a catheter for delivering a plurality of expansible prostheses to a body lumen comprises a catheter body, a sheath, and a plurality of radially expansible prostheses. The catheter body has a proximal end and a distal end, and the sheath is coaxially disposed over the catheter body with the prostheses positionable in an annular space between the inside of the sheath and the exterior of the catheter body. The sheath is preferably retractable relative to the catheter body so that the prostheses may be advanced beyond a distal end of the sheath. Usually, the catheter will further comprise a pusher tube disposed coaxially over the catheter body and within an interior lumen of the sheath. A distal end of the pusher tube will engage a proximal end of the proximal-most prosthesis so that the pusher tube can be distally advanced relative to the sheath to selectively push or deploy individual prostheses from the sheath. Often, such deployment is achieved by holding the pusher tube and prostheses substantially stationary relative to the body lumen while the sheath is retracted proximally to release or deploy the prostheses. Each of the pusher, sheath and catheter body may have a lubricious inner surface and/or a lubricious outer surface.

Usually, at least a distal portion of the sheath will have a greater column strength than that of a distal portion of the catheter body. Additionally or alternatively, the pusher tube may also have a greater column strength than a distal portion of a catheter body. By providing column strength in the outer most portion of the catheter, i.e., the sheath, and optionally the pusher tube, the overall column strength of the catheter can be increased with a minimum increase in its diameter or profile. It will be appreciated that low profile catheters are highly advantageous for accessing remote regions of the vasculature, particularly the small coronary and cerebral arteries. Using the preferred constructions of the present invention, catheters having diameters 2 mm or less, and in some instances as low as 1 mm or less, can be achieved. The constructions will, of course, also be suitable for larger diameter catheters for use in the peripheral and other larger blood vessels.

The catheter of the present invention will preferably carry at least two prostheses, more preferably carrying at least three prostheses, and often carrying a greater number of prostheses as set forth above in connection with other embodiments. The prostheses will typically be arranged in an end-to-end manner either with or without a physical linkage therebetween. The physical linkage may comprise a frangible component which must be mechanically broken or alternatively may comprise a pair of coupling elements which fit together and which may be separated without any material breakage. Frangible coupling elements will usually comprise a strut, bar, spring, or similar connecting link and will optionally be scored, notched, or otherwise adapted to break along a particular line when a suitable mechanical force is applied. Exemplary separable coupling elements include male and female elements, such as a rod and tube which may be axially separated, a tab and receptacle which may be radially separated, and the like.

In a specific embodiment of the catheter, the catheter body may comprise an expansion element, such as an inflatable balloon, near its distal end. The expansion element will be positionable distal to the retractable sheath so that it can be used to regularly expand one or more of the prostheses. For example, the inflatable balloon may have a lubricious outer surface and carry multiple prostheses on its outer surface so that sheath retraction can expose one, two, three, or more of the prostheses. The remaining prostheses will continue to be covered by the sheath. When inflating the balloon, however, only that portion of the balloon and those prostheses carried on the exposed portion of the balloon will be inflated. The remaining (proximal) portion of the balloon will continue to be constrained by the sheath so that neither the balloon nor the prostheses covered by the sheath will be expanded. In this way, any preselected number of the individual prostheses may be expanded at one time, while the remaining prostheses are protected and unexpanded, remaining available for subsequent expansion using the balloon.

Alternatively or in addition to the balloon, the catheter body may comprise a heater for selectively heating prostheses which have been advanced distally beyond the sheath. For example, the catheter body may have a lumen for delivering a heated medium, such as heated saline, intravascularly to heat and expand stents or other prostheses formed from suitable heat memory alloys (as described in more detail below). Alternatively, a separate exterior guide catheter or other tube may be used for delivering such a heated medium to effect expansion of the prostheses. As a third alternative, a powered heating element, such as a radio frequency heater, electrical resistance heater, or laser-heated element, may be provided on the catheter body for directly heating the exposed prostheses.

For the delivery of individual prostheses or stents which are joined by frangible or breakable links, as discussed above, it will often be desirable to provide a shearing mechanism on the catheter. The shearing mechanism will usually be mechanical, but could also be electrolytic, ultrasonic, or chemical. In the exemplary embodiments, the shearing mechanism comprises a first shearing element on a distal region of the catheter body and a second or mating shearing element on a distal region of the sheath. The prostheses may be advanced from the sheath while the shearing mechanism on the catheter body is distally advanced (leaving a space or opening for prosthesis deployment). After a desired number of prostheses have been deployed, the catheter body may be retracted relative to the sheath in order to close the shearing elements to sever the link(s) between the advanced prostheses and those prostheses which remain within the sheath. In other cases, the shearing mechanism could be an electrode for inducing electrolytic breakage of the link, an ultrasonic transducer for mechanically degrading a susceptible link (i.e. a link having a resonant frequency which corresponds to the ultrasonic transducer), a luminal port for releasing a chemical agent selected to chemically degrade the link, or the like.

In a further alternative embodiment, a catheter constructed in accordance with the principles of the present invention comprises a pusher tube, a plurality of radially expansible prostheses arranged end-to-end and extending distally of the distal end of the pusher tube, and a sheath disposed coaxially over the pusher tube and the prostheses. Optionally, but not necessarily, this embodiment will include a catheter body disposed coaxially within the pusher tube and prostheses. By retracting the sheath proximally relative to the pusher tube, individual ones or groups of the prostheses will be exposed and deployed. The catheter body may be used in any of the ways described previously in order to effect or control deployment of the prostheses. Optionally, the pusher tube, the sheath, or both, may have a greater column strength than the catheter body when the catheter body is employed.

Systems of detachable expansible prostheses according to the present invention include a plurality of ring-like radially expansible prostheses arranged end-to-end along an elongate axis. At least one pair of coupling elements join each pair of adjacent prostheses, where the coupling elements physically separate without fracture in response to axial tension or differential radial expansion. The coupling elements, however, remain coupled when subjected to axial compression such as may occur as the prostheses are axially advanced within a body lumen or elsewhere. The prostheses may be composed of a malleable material so that they will be expansible in response to an internally applied radially expansive force, such as a balloon expansion force applied by a balloon carried by the catheter body in any of the prior embodiments of the present invention. Alternatively, the prostheses may be composed of a resilient material, such as spring stainless steel, nickel-titanium alloy; or the like, so that they may be "self-expanding," i.e. expand when released from radial constraint. As a third alternative, the prostheses may be composed of a heat memory alloy, such as a nickel titanium alloy, so that they may be induced to expand upon exposure to a temperature above body temperature. Materials suitable for forming each of these three types of prostheses are well described in the patent and medical literature.

In specific examples of the systems, the coupling elements may be male and female so that they decouple upon the application of an axial force. For example, the coupling elements may be a rod and a tube having a central passageway for receiving the rod. Alternatively, the coupling elements may be configured to decouple upon differential radial expansion. For example, a first coupling element may extend from the end of a first prostheses and have an enlarged portion or end. By providing a cut-out in the adjacent prostheses having a periphery which matches the periphery of the extension on the first prostheses, coupling elements can be mated and locked together. The locking will resist axial separation, but permit radial separation when one of the prostheses is radially expanded.

The systems of prostheses just described may be preferably employed with any of the catheter delivery systems described previously.

The present invention further provides methods for stenting extended lengths of the body lumen, where the methods comprise introducing a catheter carrying a plurality of radially expansible prostheses to a target site within the body lumen. The prostheses are arranged end-to-end and are covered by a sheath. The prostheses are then deployed by retracting the sheath relative to the prostheses by a first preselected distance to uncover a first predetermined number of the prostheses. After retraction of the sheath, a first predetermined number of prostheses, which may be anywhere from one up to the entire number of prostheses being carried, are radially expanded at the target site within the target site of the body lumen.

Prosthesis expansion may be achieved in a variety of ways. In a first instance, the prostheses are expanded by inflating a balloon within the particular prosthesis to be expanded. For example, a single balloon may be disposed under all the prostheses, with the sheath retracted to expose only those prostheses to be deployed. When the balloon is expanded, the balloon will expand the exposed prostheses, with expansion of the prostheses which remain covered being restrained by the sheath. By further retracting the sheath, the previously undeployed prostheses may then be deployed. Optionally, the prostheses are advanced (or at least axially restrained relative to the sheath) by a pusher tube which engages a proximal end of the proximal-most prosthesis.

As an alternative to balloon expansion, the uncovered prostheses may be expanded by exposure to heat. The heat may be applied by directing a heated medium to the prostheses, directing electrical energy through the prostheses, and/or energizing a heating element positioned adjacent to the uncovered prostheses.

In preferred aspects of the methods of the present invention, the body lumen will be a blood vessel, preferably a coronary artery, a cerebral artery, or other small artery. The prostheses will preferably be coated with biologically active or inert agent, such as an agent selected to inhibit hyperplasia, more specifically being any of the particular agents set forth hereinabove.

The catheters of the present invention will comprise a number of coaxial components, such as sheaths, pusher tubes, catheter bodies, and the like. While it will often be described that stents or other prostheses are advanced distally from the sheath, such description will apply to sheaths which are retracted proximally relative to the prostheses to effect the release. Thus, all descriptions of direction are meant to be relative.

BRIEF DESCRIPTION OF THE DRAWINGS

FIGS. 8A-8C illustrate a catheter and its use for delivering self-expanding prostheses according to the methods of the present invention.

FIGS. 9A and 9C illustrate an alternative catheter construction intended for delivering self-expanding prostheses according to the methods of the present invention.

FIGS. 10A-10C illustrates use of the catheter for delivering prostheses by a heat-induction method in accordance with the principles of the present invention.

FIGS. 12A-12D illustrate a catheter for delivering multiple prostheses using balloon expansion in accordance with the methods of the present invention.

FIGS. 13A-13D illustrate a catheter including a stent valve for delivering multiple prostheses using balloon expansion in accordance with the methods of the present invention.

DETAILED DESCRIPTION OF THE SPECIFIC EMBODIMENTS

Figure 1:
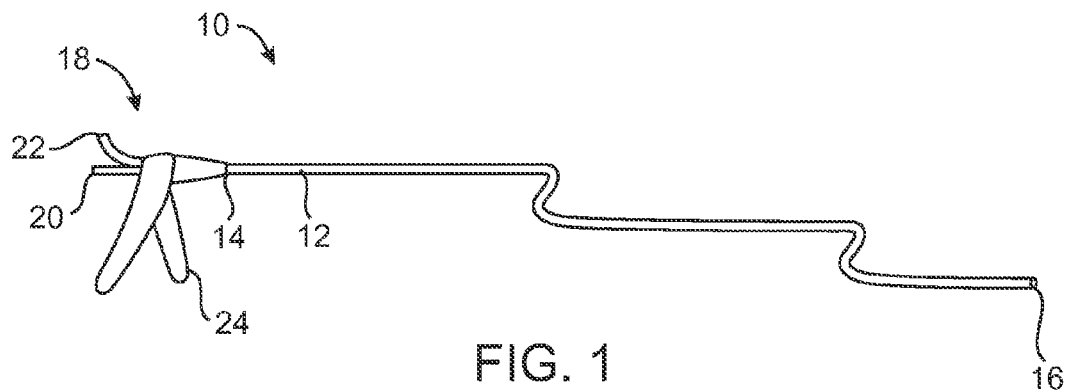
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body is formed from a conventional catheter material, such as braided or coiled stainless steel, a natural or synthetic polymer, including silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French.

Figure 2:
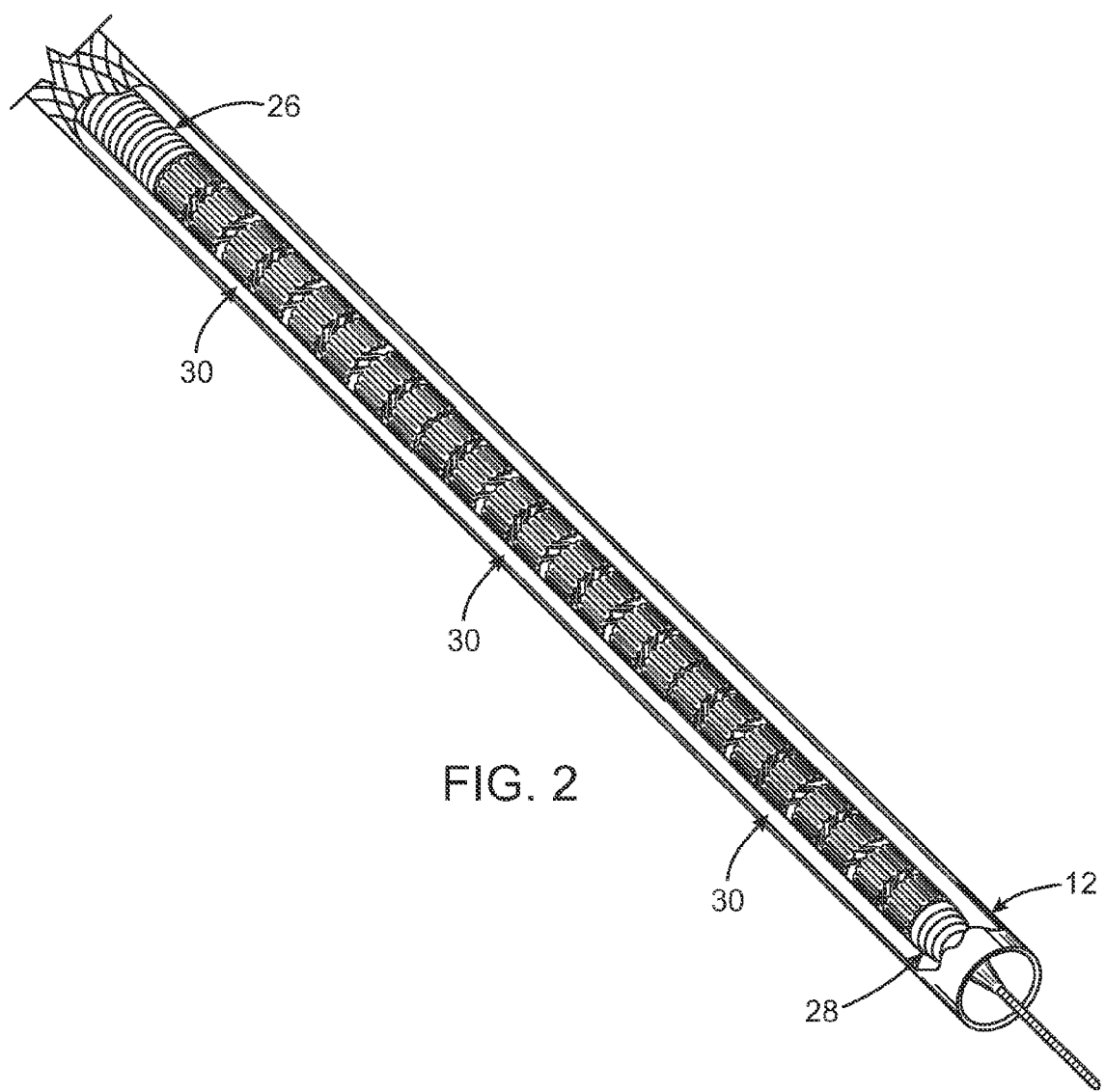
FIG. 2 is a detailed view of the distal end of the catheter of FIG. 1 with portions broken away.

Catheter 10 will include a handle 18 at its proximal end 14. The handle may include a guidewire port 20 and a balloon inflation port 22, as well as a handle grip 24 which advances a pusher shaft whose distal end 26 is shown in FIG. 2. Additionally, the handle permits reciprocation of a catheter delivery balloon 28, also shown in FIG. 2.

A plurality of stents 30 are carried in a lumen of the catheter body 12, as shown in FIG. 2. While three stents 30 are shown, it will be appreciated that additional stents may be carried generally within the ranges disclosed above. The illustrated stents comprise a plurality of serpentine ring structures joined by offset struts. It will be appreciated, however, that a wide variety of stent structures could be carried by the catheter 10, generally as described above.

Figure 3A:
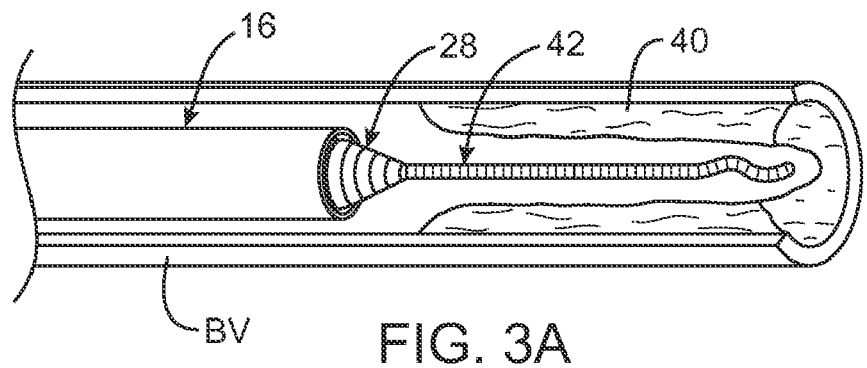
FIGS. 3A-3F illustrate use of the catheter of FIG. 1 for deploying a plurality of stents using balloon expansion.
Figure 3B:
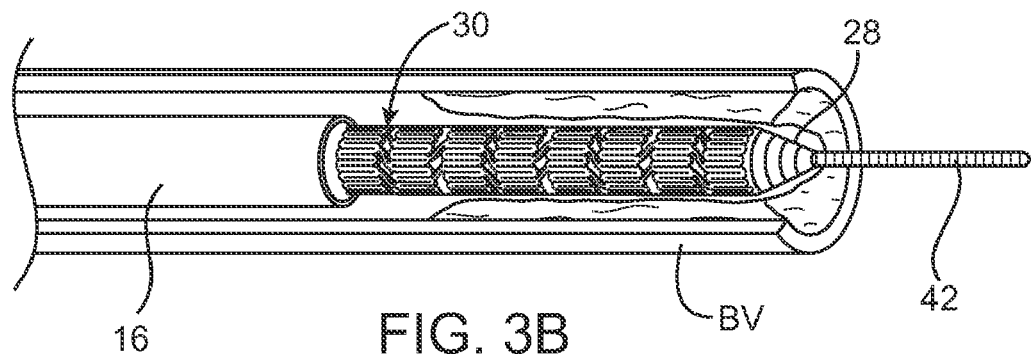
Figure 3C:
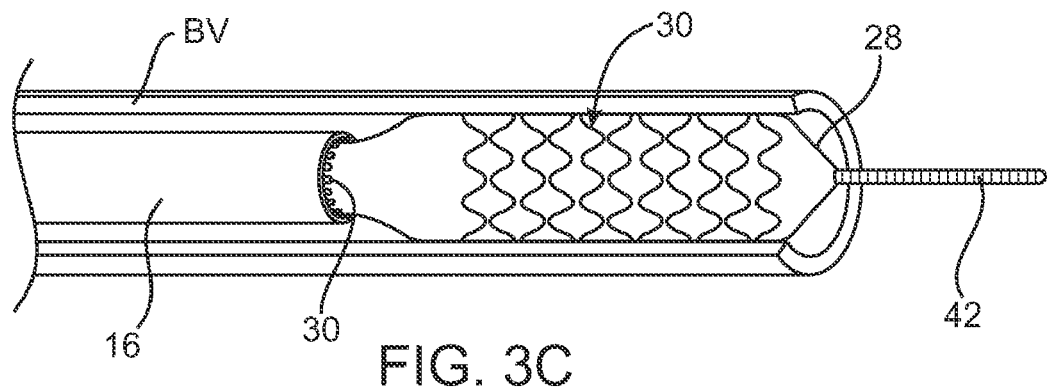

Referring now to FIGS. 3A-3F, the distal end 16 of the catheter 10 is advanced to target location 40 within a diseased blood vessel (BV) over a guidewire 42, as illustrated in FIG. 3B. Balloon 28 carries a first of the three stents 30, and is advanced distally from the catheter to deploy the stent within the treatment region 40, as illustrated in FIG. 3B (optionally by retracting the catheter body 12 proximally relative to balloon 28). Once the stent 30 is properly located, the balloon 28 is inflated to deploy the stent (and optionally dilate the treatment region), as illustrated in FIG. 3C.

Figure 3D:
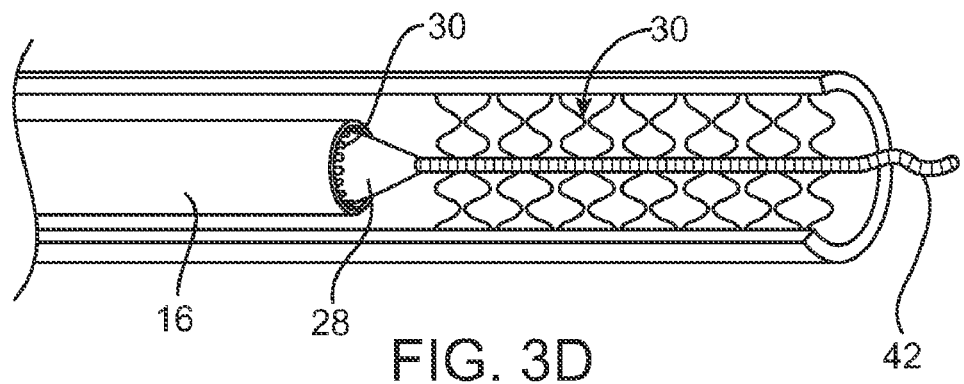
Figure 3E:
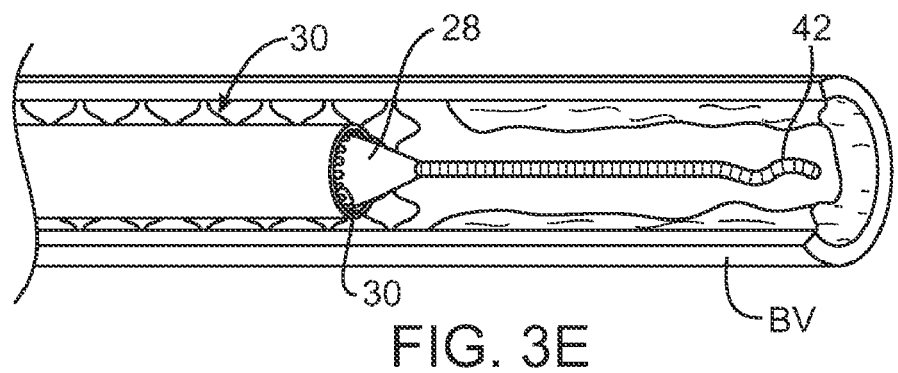
Figure 3F:
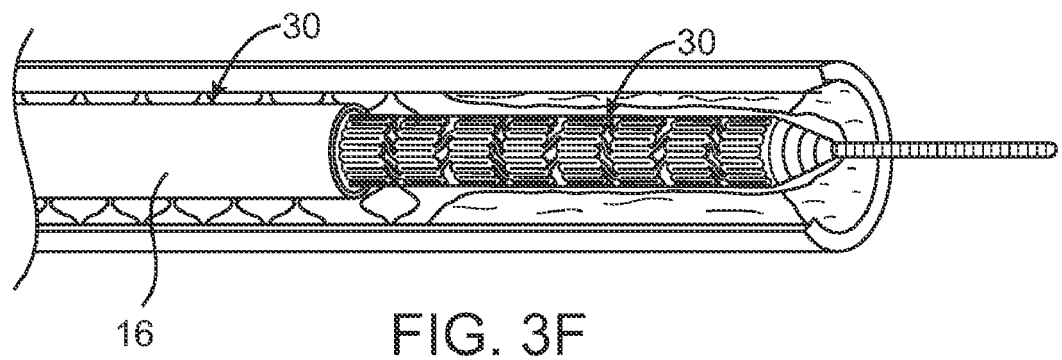

The balloon is then deflated, and retracted back into the distal end of the catheter 16, as illustrated in FIG. 3D. The expanded stent is left in place. The balloon 28 is retracted back to within the second stent 30, as illustrated in FIG. 3E. The second stent has been advanced using the pusher 26 so that it is properly located over the balloon 28, and the distal end of the catheter 16 may then be advanced so that the second stent 30 is located within a second treatment region spaced apart from the first treatment region. As illustrated in FIG. 3F, the treatment regions are adjacent to each other. It will be appreciated, however, that the second treatment region could be spaced a substantial distance from the first treatment region. Deployment of the second stent 30 is then completed in the same manner as described above for the first stent. Similarly, deployment of third, fourth, fifth, and additional stents 30 may be effected in the same manner. In this way, it will be appreciated that relatively lengthy and/or disseminated regions within a blood vessel may be treated.

Figure 4:
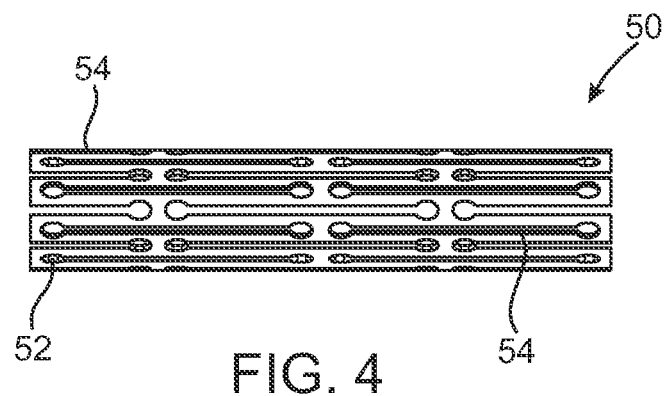
FIG. 4 illustrates an exemplary prosthesis constructed in accordance with the principles of the present invention.

Referring now to FIG. 4, an exemplary prosthesis 50 constructed in accordance with the principles of the present invention is illustrated. The prosthesis has a tubular body 52 having a plurality of axial slots 54, typically formed by laser cutting or chemical etching a tubular stock, such as stainless steel or nickel-titanium hypotube. Prosthesis 50, which may be delivered in groups of two, three, four, or more in accordance with the principles of the present invention, will have a length within the ranges set forth above. The diameter, prior to expansion, will typically be below 2 mm, preferably being below 1 mm, although in some instances much larger diameters can be used. The diameter of the prosthesis 50 upon expansion, of course, will be much greater, typically being at least twice as large, sometimes being at least three times as large, or even larger.

Figure 5A:
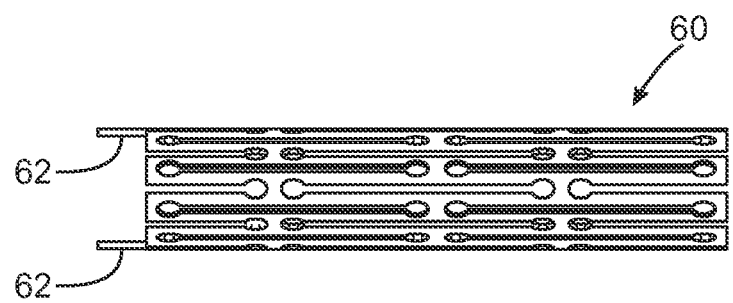
FIGS. 5A and 5B illustrate a prosthesis similar to that shown in FIG. 4, but further including coupling elements for permitting detachable coupling of adjacent prostheses.
Figure 5B:
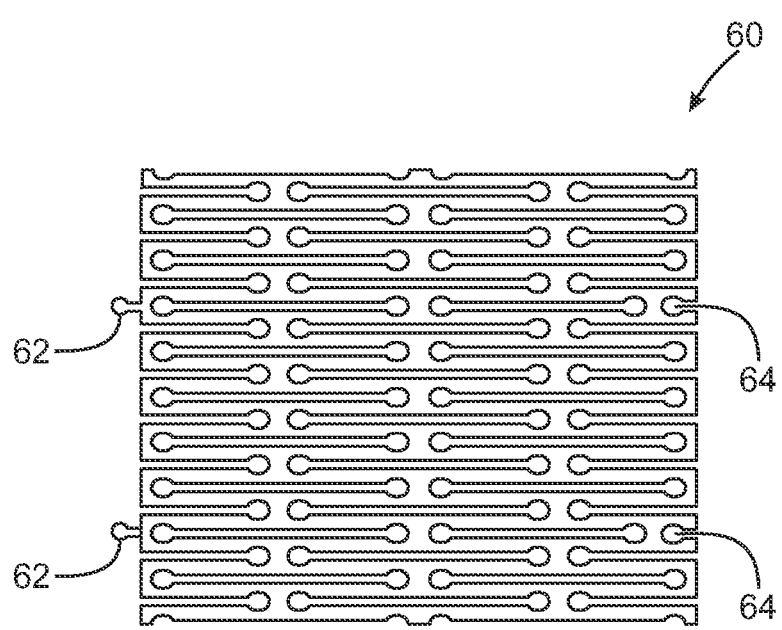

Referring now to FIGS. 5A and 5B, a prosthesis 60, similar to prosthesis 50, includes a pair of coupling elements 62 which are received in mating slots 64. FIG. 5B is a "rolled-out" view of the prosthesis 60 for better illustrating the coupling element 62 and slots 64 of the prosthesis 60.

Figure 5C:
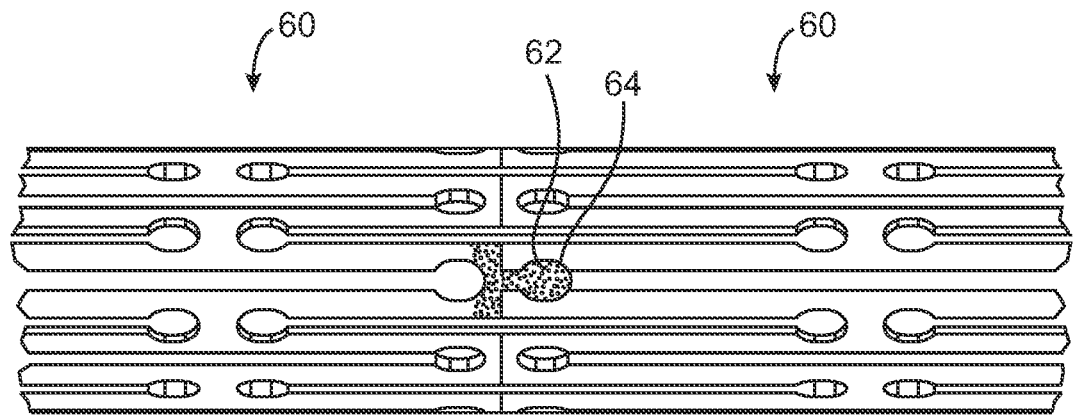
FIG. 5C illustrates a pair of prostheses, as shown in FIG. 5A and FIG. 5B, joined together by the coupling elements.

As shown in FIG. 5C, pairs of prosthesis 60 may be joined or coupled by circumferentially aligning the coupling element 62 with the slot 64. Although only a single coupling element 62 and slot 64 is visible in FIG. 5C, it will be appreciated that the second coupling element and slot will be located on the opposite side of the illustrated pair of prostheses.

Figure 5D:
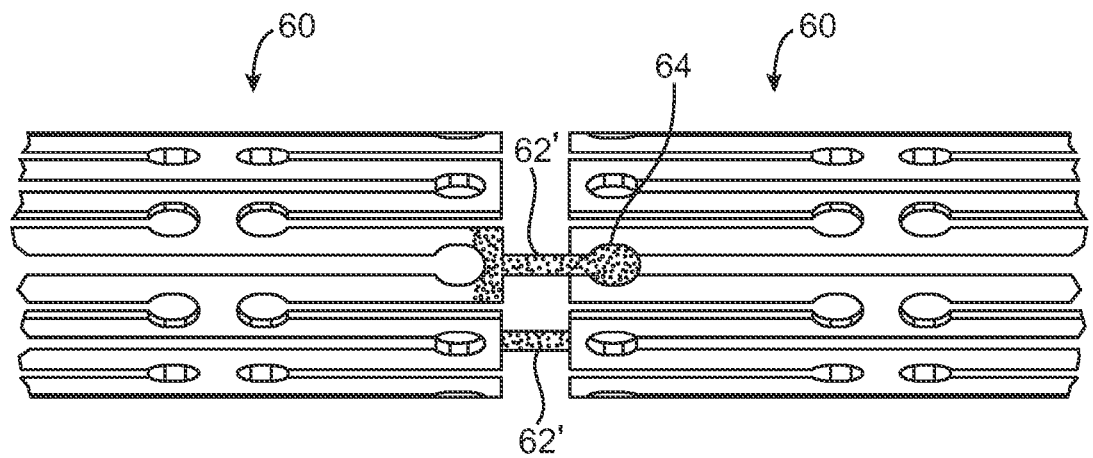
FIG. 5D illustrates a pair of adjacent prostheses coupled by a modified coupling element.

In FIG. 5C, the two prosthesis 60 are abutted directly against each other. Such a configuration is advantageous in that it provides for a substantially continuous stent or graft structure when the pair is expanded together in a body lumen. The structure, however, is disadvantageous in that it does not provide for flexibility at the point where the two prostheses meet. In order to provide for greater flexibility, as shown in FIG. 5D, a coupling element 62' can have an elongated shank to provide for a desired offset, typically in the range from 0.05 mm to 1 mm, preferably from 0.1 mm to 0.5 mm.

Figure 5E:
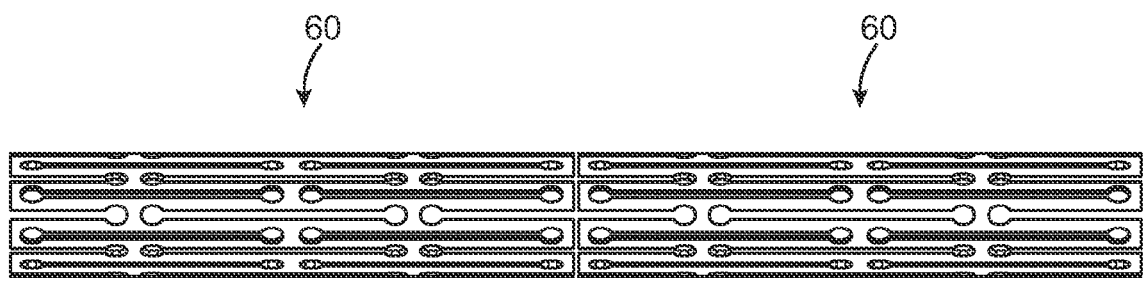
FIGS. 5E and 5F illustrate radial separation of the adjacent prostheses of FIG. 5C.
Figure 5F:
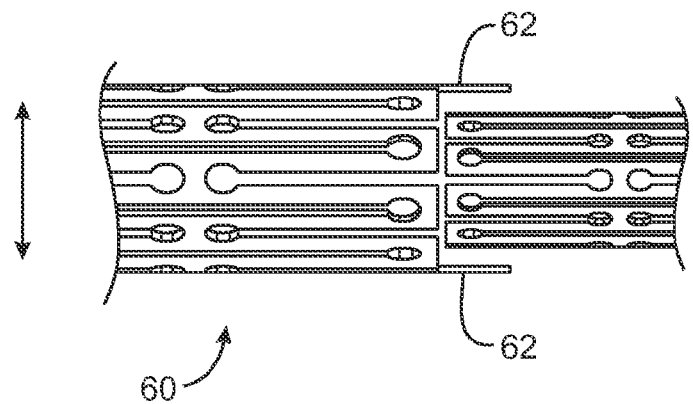

Referring now to FIGS. 5E and 5F, axial separation of the prostheses 60 is achieved by differential radial expansion of at least one of the prostheses. For example, when both prostheses 60 are in their unexpanded configurations, as shown in FIG. 5E, the coupling elements 62 are constrained by the slots 64, as previously described. By radially expanding the left-hand prostheses 60, as shown in FIG. 5F, the coupling elements 62 will be moved radially outwardly from the slots so that the two prostheses are no longer axially linked. It will be appreciated, however, that the two prostheses 60 may be radially expanded together (as described in more detail hereinafter) in a manner which preserves the link created by the coupling elements 62 and slots 64 so that combinations of two, three, four, or more prostheses may be delivered simultaneously and, in effect, provide a continuous prosthesis having a length which is some multiple of the length of each individual prostheses 60. The combined prostheses may then be separated from any additional prostheses (which remain in a delivery catheter as described below) by the radial expansion of those prostheses which are to be deployed. In this way, stents, grafts, or other prostheses may be delivered to the body lumen in both different lengths (by properly selecting the number of individual prostheses 60) and at different locations (by releasing individual or multiple prostheses 60 at different portions of the body lumen).

Figure 6A:
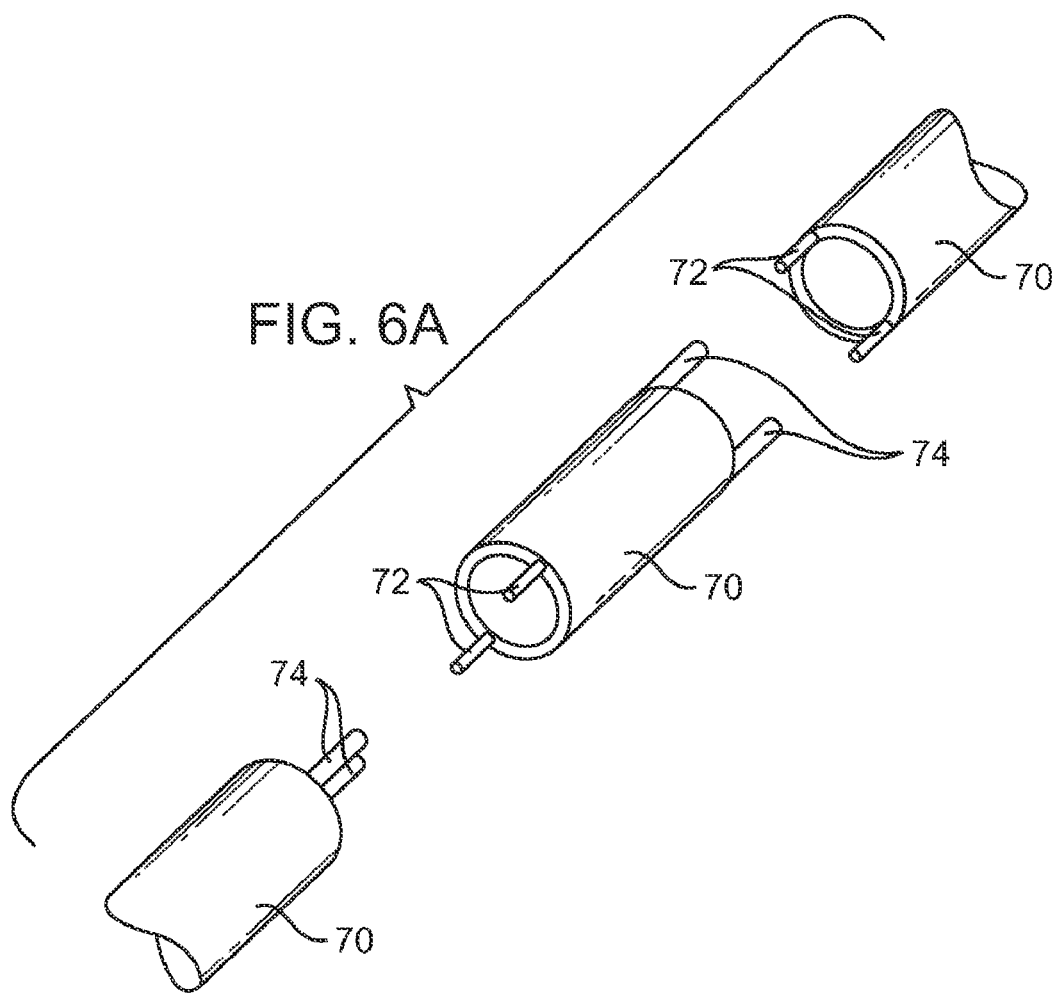
FIGS. 6A and 6B illustrate a second coupling mechanism constructed in accordance with the principles of the present invention.
Figure 6B:
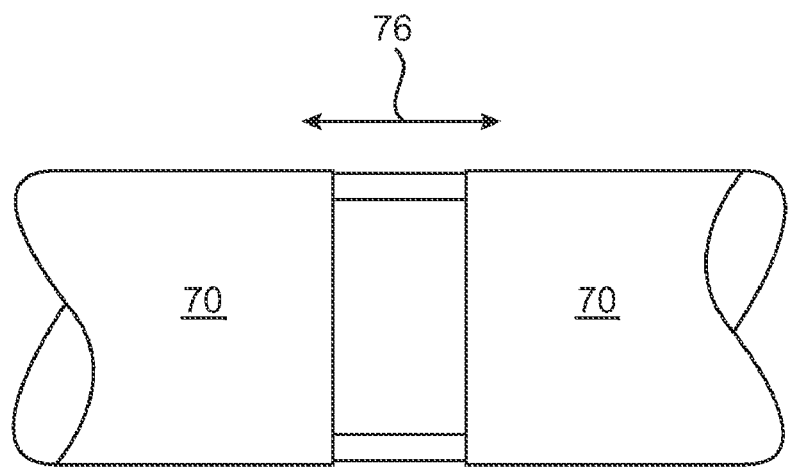

Axially separable coupling elements may also be provided, as illustrated in FIGS. 6A and 6B. Each prosthesis 70 includes a pair of male coupling elements 72 at one end and a pair of female coupling elements 74 at the other end. The male coupling elements 72 are typically short rods which extend axially from the periphery of the prosthesis end and the female coupling elements are typically short tubes having hollow interiors which detachably receive the male coupling elements. Thus, the prostheses 70 may be joined in an end-to-end manner, as shown in FIG. 6B. The prostheses are separated by pulling them in an axial direction, as shown by arrow 76, but will remain linked under axial compression as well as when exposed to a substantial bending moment. Thus, the axially separable coupling structures of FIGS. 6A and 6B are advantageous in that they remain linked during deployment of the prostheses 70, even when deployment involves significant bending and radial stress. Separation may be effected by pullback on the delivery catheter in order to disengage the coupling elements 72 and 74.

Figure 7:
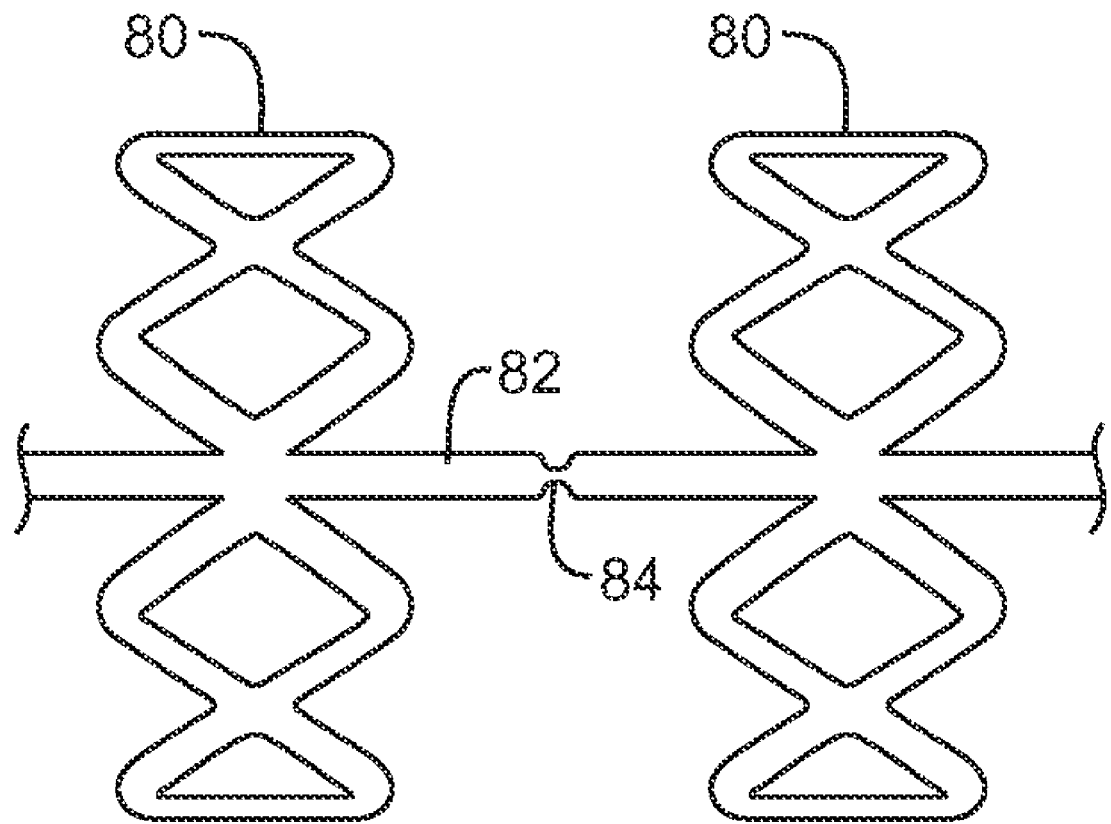
FIG. 7 illustrates a frangible linkage for joining a pair of adjacent prostheses.

A third approach for detachably coupling adjacent prostheses 80 is illustrated in FIG. 7. Each prosthesis 80 comprises an expansible ring of diamond-shaped members. Other conventional stent or prostheses structures, however, could also be used. The adjacent prostheses 80 are joined by an axial beam 82 which preferably includes a weakened segment 84 near its midpoint. The use of such a joining structure, which will require physical breakage (as opposed to the simple detachment characteristic of the embodiment of FIGS. 5 and 6) is advantageous in that it provides a very strong linkage which permits both the application of axial compression and axial tension without decoupling. The disadvantage of such a linkage is that it usually requires some mechanism or capability to be incorporated in the delivery catheter to permit selective breakage of the couple.

Referring now to FIGS. 8A-8C, a catheter 100 suitable for delivering a plurality of self-expanding prostheses 102 will be described. Catheter 100 comprises a sheath 104 having an axial lumen which carries the prostheses 102 near its distal end 106. A pusher tube 108 is also positioned in the lumen and is located proximally of the proximal most prosthesis 102. The individual prostheses 102 may be delivered into a body lumen, typically a blood vessel BV, as illustrated in FIG. 8B. The catheter is introduced over a guidewire GW to a desired target site in the blood vessel BV. When at the target site, a first of the prostheses 102 is deployed by axially advancing the pusher tube 104 so that the line of prostheses 102 is axially advanced, with the distal-most prostheses being released from the distal end 106 of the catheter. As it is released, the distal-most prostheses 102 expands since it is being released from the radial constraint provided by the sheath 104.

Figure 9C:
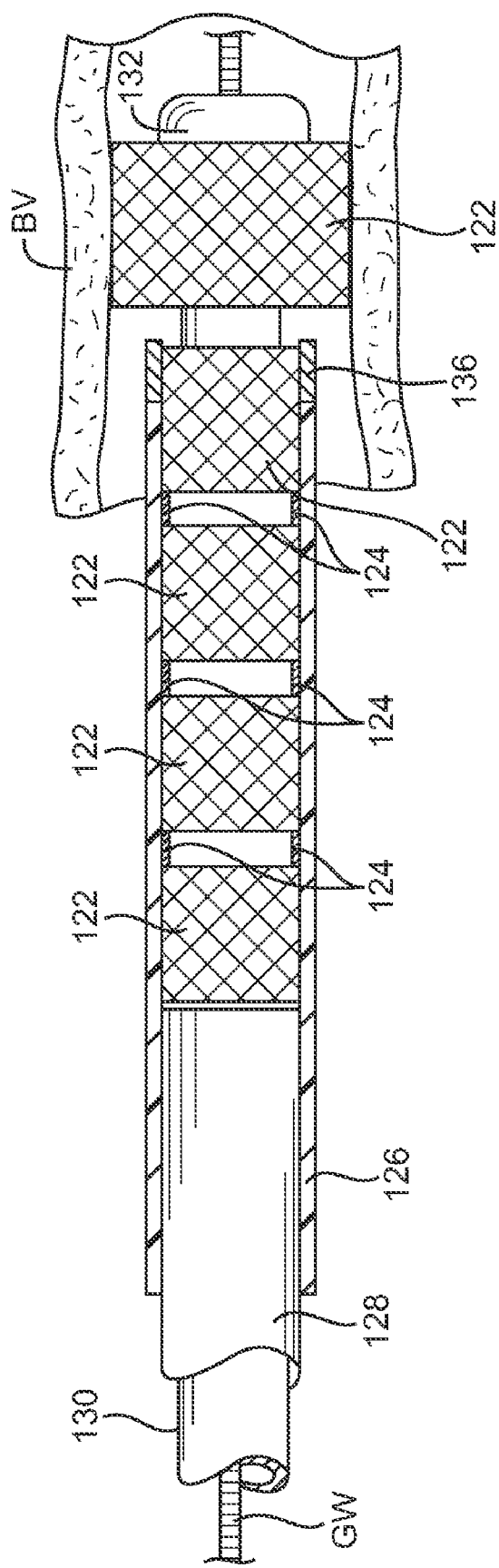

Catheter 100 of FIGS. 8A-8C is intended for delivering prostheses which abut each other in an end-to-end manner, but which are otherwise unconnected. A catheter 120 intended for releasing self-expanding prostheses 122 which are mechanically linked by frangible coupling elements 124 is illustrated in FIGS. 9A-9C. The prostheses 122 and coupling elements 124 may be similar to the prosthesis structure shown in FIG. 7, or may comprise other linked prosthesis or stent structures, for example as shown in U.S. Pat. No. 6,258,117, the disclosure of which is incorporated herein by reference.

Catheter 120 comprises a sheath 126, a pusher tube 128, and a catheter body 130 having a shearing element 132 at its distal end. Conveniently, the pusher tube 128 is coaxially received over a shaft 134 of the catheter body 130. In this way, the pusher tube may be used to axially advance each prosthesis 122 by pushing on the proximal end of the proximal-most prosthesis, as shown in FIG. 9B.

The catheter 120 is advanced over a guidewire GW to a desired target site in a blood vessel BV. After reaching the target site, at least a first prosthesis 122 is advanced from the distal end of the sheath so that it radially expands to engage an inner wall of the blood vessel. After the at least one prosthesis 122 is advanced sufficiently far, the frangible coupling elements 124 will reach a shearing element 136, typically a metal ring, disposed at the distal end of the sheath 126. By then axially retracting the catheter body 130, a chamfered surface 138 of the shearing element 132 is engaged against the shearing element 136 in order to shear the links 122, releasing the prosthesis 122, as illustrated in FIG. 9C. After deployment and release of the first prosthesis 122, additional prosthesis 122 may be released adjacent to the first prosthesis or at different, axially spaced-apart locations within the blood vessel.

Referring now to FIGS. 10A-10C, a catheter 140 for delivering a plurality of heat expansible prostheses 142 is illustrated. The prostheses 142 are composed of a heat memory alloy, such as a nickel titanium alloy, which has been programmed to remain in an unexpanded configuration when maintained at body temperature or below, and to assume an expanded configuration when exposed to temperatures above body temperature, typically temperatures above 43° C., often above 45° C. The prostheses will have coupling members which anchor successive prostheses 142 together, typically the radially separating anchors illustrated in FIGS. 5A-5F.

The catheter 140 includes a sheath 144 and a pusher tube 146. The catheter 140 is advanced to a desired target site within the blood vessel BV over a guidewire GW in a conventional manner. After the distal-most prostheses 142 has been fully advanced from the sheath 144 (usually by retracting the sheath 144 while the prostheses are held stationary relative to the blood vessel BV using the pusher tube 146), as shown in FIG. 10B, it will remain both unexpanded and attached to the next proximal prosthesis 142 which remains within the sheath. It is important that the advanced prosthesis 142 be anchored or tethered to the remaining prostheses since it has not yet been expanded and it would otherwise be lost into the lumen of the blood vessel.

After the uncovered prostheses is properly positioned, a heated medium may be introduced through a lumen of the catheter body 148 so that it flows outwardly through the interior of the distal-most prosthesis 142. By properly selecting the temperature of the heated medium, the prosthesis to be deployed can be heated sufficiently to induce radial expansion, as illustrated in FIG. 10C. By positioning the catheter body 148 so that its distal tip is coterminous with the distal tip of the sheath 144, inadvertent heating of the prostheses 142 which remain within the sheath can be avoided. After the prosthesis 142 has radially expanded, it will separate from the coupling elements 148 located on the next prosthesis which remains within the sheath 144. Additional ones or groups of prostheses 142 may then be deployed, either at the same target site or at a different target site axially spaced-apart within the lumen of the blood vessel BV.

Figure 11:
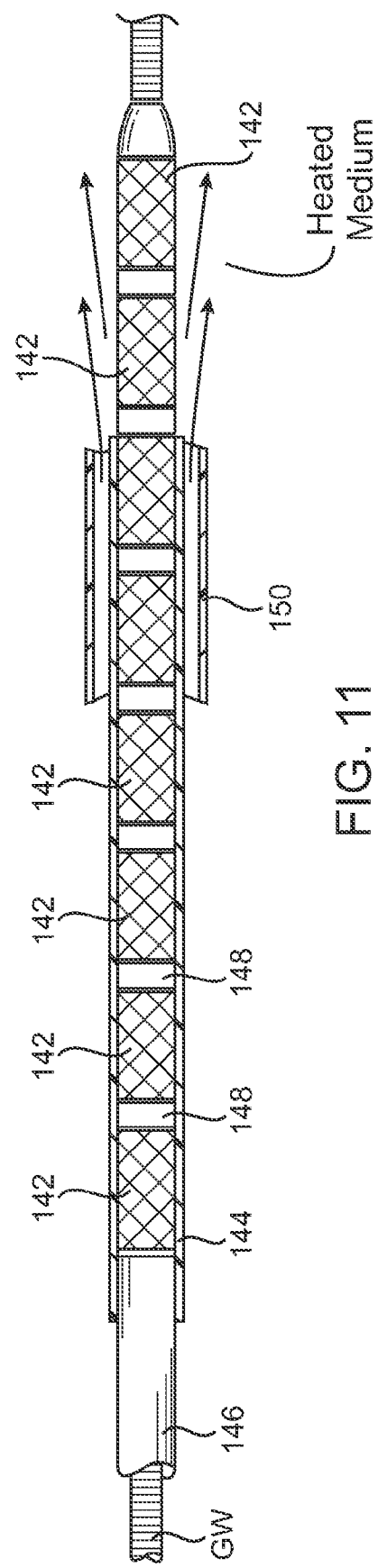
FIG. 11 illustrates an alternative catheter construction for delivering multiple prostheses via a heat-induction protocol in accordance with the principles of the present invention.

As illustrated in FIG. 11, instead of using an internal catheter body 148, as illustrated in FIGS. 10A-10C, an external sheath 150 may be used to deliver the heated medium around one or more deployed prostheses 142. Other aspects of the construction of catheter 140 may remain the same. Optionally, if the prosthesis is martensitic at body temperature, further radial expansion can be achieved by internal balloon expansion.

Figure 12D:
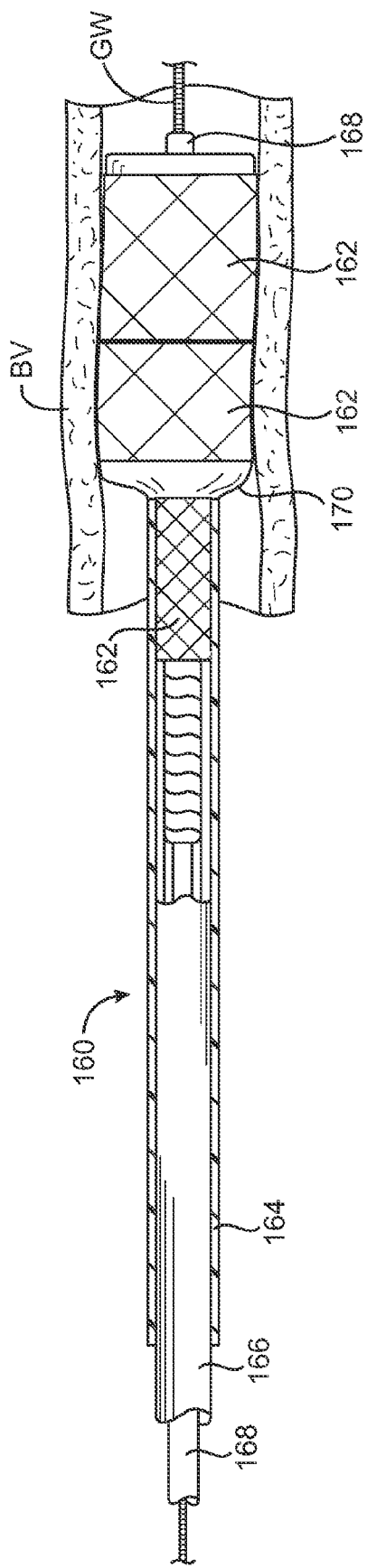

Referring now to FIGS. 12A-12D, catheter 160 intended for delivery of multiple prostheses 162 by balloon deployment is illustrated. Catheter 160 comprises a sheath 164, pusher tube 166, and a catheter body 168. The catheter body 168 includes an expansible balloon 170 over its distal portion. Individual prostheses 162 are deployed, as illustrated in FIGS. 12B and 12C, by crossing the target area with catheter 160 and then retracting sheath 164. A distal portion of the balloon 170 lies within the distal-most deployed prosthesis 162, as shown in FIG. 12B. The remaining proximal portion of the balloon 170 will, of course, remain within the other prostheses 162 which themselves remain within the sheath 164. The balloon 170 is then inflated, but only the distal portion of the balloon beyond the sheath inflates within the distal prosthesis 162, as illustrated in FIG. 12C. Expansion of the remaining proximal portion of the balloon is prevented by the sheath 164. Similarly, the remaining prostheses 162 remain unexpanded since they remain within the sheath 164. After deployment of prostheses 162, balloon 170 may be deflated and retracted into sheath 164 and remaining prostheses 162.

Referring now to FIG. 12D, additional prostheses 162 may be deployed, either at the same target location within the blood vessel or at a different, spaced-apart locations within the blood vessel. Deployment of two prostheses 162 is illustrated. The two prostheses 162 are axially exposed as the sheath is retracted over the stents which are positioned over the uninflated balloon 170. The balloon 170 is then inflated, as illustrated in FIG. 12D, thus expanding the prostheses 162 within the blood vessel BV. It will be appreciated that the catheter 160 could carry many more than the four illustrated prostheses 162, and three, four, five, ten, and even 20 or more individual prostheses could be deployed at one time, with additional single prostheses or groups of prostheses being deployed at different times and/or at different locations within the blood vessel.

Figure 13D:
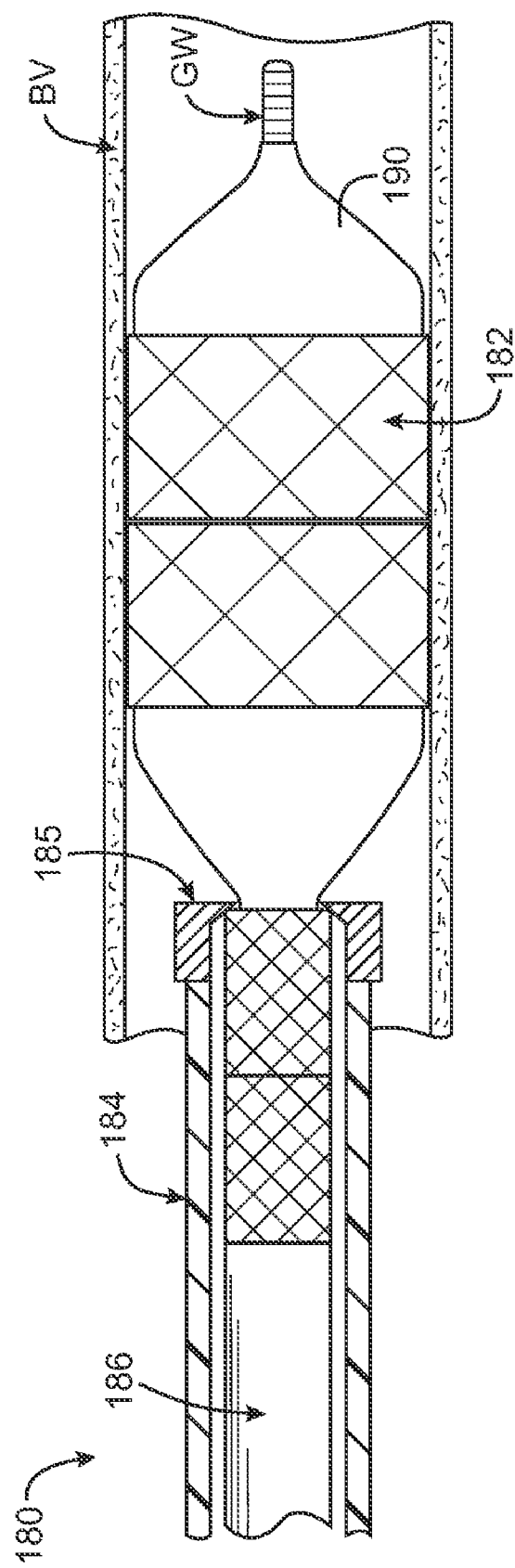

Referring now to FIGS. 13A-13D, another embodiment of a catheter 180 intended for delivery of multiple prostheses 182 by balloon deployment is illustrated. In this embodiment, catheter 180 comprises a sheath 184 having a valve member 185 at its distal end, a pusher tube 186, and a catheter body 188. The catheter body 188 includes an expansible balloon 190 over its distal portion. To deploy prostheses 182, as illustrated in FIG. 13B, a predetermined number of prostheses 182 is first exposed by retracting sheath 184 proximally (arrows) while holding pusher tube 186 in place. As shown in FIGS. 13B and 13C, valve member 185 may be used to engage a distal end of one of the prostheses 182 and the sheath 184 and the pusher tube may be retracted proximally together (arrows in FIG. 13C) to separate a proximal number of prostheses 182 from a distal number of prostheses 182. The distal portion of the balloon 190 lies within the distal, deployed prostheses 182. The remaining proximal portion of the balloon 190 will remain within the other prostheses 182 which themselves remain within the sheath 184. The balloon 190 is then inflated, as shown in FIG. 13D, but only the distal portion of the balloon inflates within the distal prostheses 182, as illustrated in FIG. 12C. Expansion of the remaining proximal portion of the balloon is prevented by the sheath 184. Similarly, the remaining prostheses 182 remain unexpanded since they remain within the sheath 184.

Referring now to FIG. 13D, single or multiple prostheses 182 may be deployed at the same target location within the blood vessel. Additional prostheses 182 may also be deployed at different, spaced-apart locations within the blood vessel. Deployment of two prostheses 182 is illustrated at one location in FIG. 13D. It will be appreciated that the catheter 180 could carry many more than the four illustrated prostheses 182, and three, four, five, ten, and even 20 or more individual prostheses could be deployed at one time, with additional single prostheses or groups of prostheses being deployed at different times and/or at different locations within the blood vessel.

Figure 14:
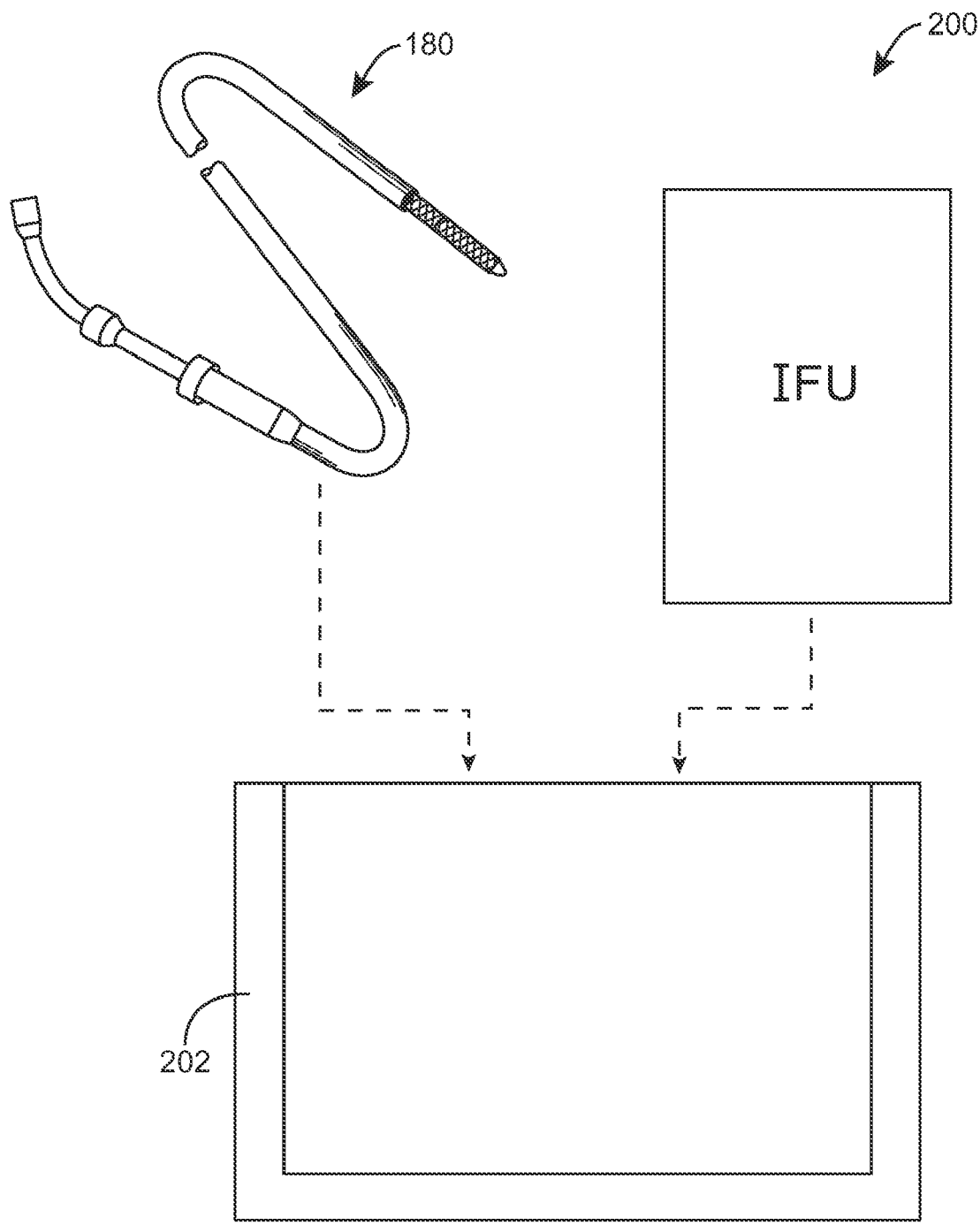
FIG. 14 illustrates an exemplary kit constructed in accordance with the principles of the present invention.

Referring now to FIG. 14, kits 200 according to the present invention comprise a catheter 160 (or any other of the illustrated catheters of the present invention) in combination with instructions for use IFU. The instructions for use set forth any of the methods of the present invention, and in particular set forth how the catheter 180 may be used to implant single or multiple prostheses within a blood vessel or other body lumen. The catheter 180 and instructions for use will typically be packaged together, for example within a conventional package 202, such as a box, tube, pouch, tray, or the like. Catheter 160 will typically be maintained in a sterile condition within the package 202. The instructions for use may be provided on a package insert, may be printed in whole or in part on the packaging, or may be provided in other ways, such as electronically over the internet, on an electronic medium, such as a CD, DVD, or the like.

The preferred embodiments of the invention are described above in detail for the purpose of setting forth a complete disclosure and for the sake of explanation and clarity. Those skilled in the art will envision other modifications within the scope and sprit of the present disclosure.

What is claimed is:

1. An apparatus for treating a body lumen comprising:
a flexible catheter shaft having proximal and distal ends;
an expandable member attached to the catheter shaft near the distal end, the expandable member being expandable to an expanded configuration having an expanded length; and
a radially-expandable tubular prosthesis comprising a plurality of discrete stents, the prosthesis releasably coupled to the catheter shaft, a deployed portion of the prosthesis being expandable to a deployed configuration having a deployed length;
wherein the expanded length and the deployed length are each selectively changeable from the proximal end of the catheter shaft, and
wherein the deployed length of the prosthesis comprises two or more discrete stents radially expandable at the same time while at least one stent remains unexpanded and coupled to the catheter shaft, and wherein the expanded length is expanded while a portion of the expandable member remains unexpanded.

2. The apparatus of claim 1, further comprising:
a first adjustment mechanism controllable from the proximal end of the catheter shaft for selectively changing the expanded length; and
a second adjustment mechanism controllable from the proximal end of the catheter shaft for selectively changing the deployed length.

3. The apparatus of claim 2, wherein the first adjustment mechanism comprises a sheath having a distal extremity axially movable over the expandable member and a proximal extremity extending to the proximal end of the catheter shaft, the distal extremity being adapted to constrain a proximal portion of the expandable member from expanding while a distal portion of the expandable member is expanded.

4. The apparatus of claim 2, wherein the second adjustment mechanism comprises a pusher member axially movable along the catheter shaft and adapted to apply a distally-directed force to the prosthesis.

5. The apparatus of claim 1, further comprising a sheath having a distal extremity axially movable over the expandable member and a proximal extremity extending to the proximal end of the catheter shaft, the distal extremity being adapted to constrain a proximal portion of the expandable member from expanding while a distal portion of the expandable member is expanded.

6. The apparatus of claim 1, further comprising a pusher member axially movable relative to the expandable member and adapted to apply a distally-directed force to the prosthesis.

7. The apparatus of claim 1, wherein the expanded length may be selectively changed independently of the deployed length.

8. The apparatus of claim 1, further comprising a mechanism controllable from the proximal end of the catheter shaft for selectively changing both the expanded length and the deployed length.

9. The apparatus of claim 1, wherein the prosthesis segments are unconnected to each other before radially expanding.

10. An apparatus for treating a body lumen comprising:
a flexible catheter shaft positionable in the body lumen and having proximal and distal ends;
an expandable member attached to the catheter shaft near the distal end, the expandable member being expandable to an expanded configuration having an expanded length;
a radially-expandable tubular prosthesis comprising a plurality of discrete stents, the prosthesis releasably coupled to the catheter shaft, a deployed portion of the prosthesis being expandable to a deployed configuration having a deployed length;

a first adjustment mechanism controllable from the proximal end for selectively changing the expanded length without removing the catheter shaft from the body lumen, wherein the expanded length is expanded while a portion of the expandable member remains unexpanded; and a second adjustment mechanism controllable from the proximal end for selectively changing the deployed length without removing the catheter shaft from the body lumen, wherein the deployed length of the prosthesis comprises two or more discrete stents radially expandable at the same time while at least one stent remains unexpanded and coupled to the catheter shaft.

11. The apparatus of claim 10, wherein the first adjustment mechanism comprises a sheath having a distal extremity axially movable over the expandable member and a proximal extremity extending to the proximal end of the catheter shaft, the distal extremity being adapted to constrain a proximal portion of the expandable member from expanding while a distal portion of the expandable member is expanded.

12. The apparatus of claim 10, wherein the second adjustment mechanism comprises a pusher member axially movable along the catheter shaft and adapted to apply a distally-directed force to the prosthesis.

13. The apparatus of claim 10, wherein the prosthetic segments are unconnected to each other before radially expanding.

14. An apparatus for treating a body lumen comprising:
a flexible catheter shaft positionable in the body lumen and having proximal and distal ends;
an expandable member attached to the catheter shaft near the distal end, the expandable member being expandable to an expanded configuration having an expanded length, wherein the expanded length is expanded while a portion of the expandable member remains unexpanded; and a plurality of radially-expandable and discrete tubular prostheses releasably coupled to the catheter shaft, the prostheses being separable from each other to allow a first group of two or more of the discrete prostheses to be expanded at the same time while at least a second prosthesis remains unexpanded on the catheter shaft;

wherein the expanded length and the number of prostheses in the first group are each selectively changeable from the proximal end without removing the catheter shaft from the body lumen.

15. The apparatus of claim 14, further comprising a sheath having a distal extremity axially movable over the expandable member and a proximal extremity extending to the proximal end of the catheter shaft, the distal extremity being adapted to constrain a proximal portion of the expandable member from expanding while a distal portion of the expandable member is expanded.

16. The apparatus of claim 14, further comprising a pusher member axially movable relative to the expandable member and adapted to apply a distally-directed force to the prostheses.

17. The apparatus of claim 14, wherein the expanded length may be selectively changed independently of the number of prostheses in the first group.

18. The apparatus of claim 14, further comprising a mechanism controllable from the proximal end of the catheter shaft for selectively changing both the expanded length and the number of prostheses in the first group.

19. The apparatus of claim 14, wherein the prostheses are unconnected to each other before radially expanding.

20. The apparatus of claim 14, wherein the prostheses are adapted to be radially expanded by the expandable member.

21. The apparatus of claim 14, wherein the expandable member is expandable without expanding the prostheses.

* * * * *